US011475570B2

(12) United States Patent
Krummen et al.

(10) Patent No.: US 11,475,570 B2
(45) Date of Patent: Oct. 18, 2022

(54) COMPUTATIONAL SIMULATIONS OF ANATOMICAL STRUCTURES AND BODY SURFACE ELECTRODE POSITIONING

(71) Applicants: THE REGENTS OF THE UNIVERSITY OF CALIFORNIA, Oakland, CA (US); VEKTOR MEDICAL, INC., Carlsbad, CA (US)

(72) Inventors: David Krummen, Oakland, CA (US); Christopher Villongco, Carlsbad, CA (US)

(73) Assignees: The Regents of the University of California, Oakland, CA (US); Vektor Medical, Inc., Carlsbad, CA (US)

( * ) Notice: Subject to any disclaimer, the term of this patent is extended or adjusted under 35 U.S.C. 154(b) by 0 days.

(21) Appl. No.: 16/785,530

(22) Filed: Feb. 7, 2020

(65) Prior Publication Data
US 2020/0245935 A1    Aug. 6, 2020

Related U.S. Application Data

(63) Continuation of application No. PCT/US2019/040740, filed on Jul. 5, 2019.
(Continued)

(51) Int. Cl.
*G06T 7/00* (2017.01)
*G16H 50/20* (2018.01)
(Continued)

(52) U.S. Cl.
CPC ............ *G06T 7/0016* (2013.01); *A61B 5/055* (2013.01); *A61B 5/25* (2021.01); *A61B 5/291* (2021.01);
(Continued)

(58) Field of Classification Search
CPC ............... G06T 7/0016; G06T 2200/04; G06T 2207/30004; A61B 5/25; A61B 5/291;
(Continued)

(56) References Cited

U.S. PATENT DOCUMENTS 5,273,038 A   12/1993 Beavin
6,501,979 B1  12/2002 Manning et al.
(Continued)

FOREIGN PATENT DOCUMENTS

WO   WO2004102482 A1   11/2004
WO   WO-2005072607 A1   8/2005
(Continued)

OTHER PUBLICATIONS

Aguado-Sierra, J., et. al. "Patient-specific modeling of dyssynchronous heart failure: a case study." *Progress in Biophysics and Molecular Biology*, vol. 107 No. 1, 2011, pp. 147-55.
(Continued)

*Primary Examiner* — Sanjay Cattungal
(74) *Attorney, Agent, or Firm* — Mintz Levin Cohn Ferris Glovsky and Popeo, P.C.

(57) ABSTRACT

A method may include identifying a simulated three-dimensional representation corresponding to an internal anatomy of a subject based on a match between a computed two-dimensional image corresponding to the simulated three-dimensional representation and a two-dimensional image depicting the internal anatomy of the subject. Simulations of the electrical activities measured by a recording device with standard lead placement and nonstandard lead placement may be computed based on the simulated three-dimensional representation. A clinical electrogram and/or a clinical vectorgram for the subject may be corrected based on a difference between the simulations of electrical activities to account for deviations arising from patient-specific lead placement as well as variations in subject anatomy and pathophysiology.

43 Claims, 13 Drawing Sheets

Related U.S. Application Data

(60) Provisional application No. 62/694,401, filed on Jul. 5, 2018.

(51) Int. Cl.

| | | |
|---|---|---|
| *G16H 30/40* | (2018.01) | |
| *A61B 5/055* | (2006.01) | |
| *G16H 50/50* | (2018.01) | |
| *A61B 5/00* | (2006.01) | |
| *A61B 6/03* | (2006.01) | |
| *A61B 6/00* | (2006.01) | |
| *A61B 5/25* | (2021.01) | |
| *A61B 5/291* | (2021.01) | |
| *A61B 5/318* | (2021.01) | |
| *A61B 5/24* | (2021.01) | |
| *A61B 5/283* | (2021.01) | |

(52) U.S. Cl.
CPC ............. *A61B 5/318* (2021.01); *A61B 5/684* (2013.01); *A61B 5/7267* (2013.01); *A61B 6/032* (2013.01); *A61B 6/463* (2013.01); *A61B 6/467* (2013.01); *A61B 6/50* (2013.01); *A61B 6/505* (2013.01); *A61B 6/5247* (2013.01); *G16H 30/40* (2018.01); *G16H 50/20* (2018.01); *G16H 50/50* (2018.01); *A61B 5/24* (2021.01); *A61B 5/283* (2021.01); *A61B 2560/063* (2013.01); *G06T 2200/04* (2013.01); *G06T 2207/30004* (2013.01)

(58) Field of Classification Search
CPC ....... A61B 5/318; A61B 5/684; A61B 5/7267; A61B 6/032; A61B 6/463; A61B 6/467; A61B 6/50; A61B 6/505; A61B 6/5247; A61B 5/055; A61B 5/24; A61B 5/283; A61B 2560/063; A61B 5/389; G16H 50/50; G16H 50/20; G16H 30/40
See application file for complete search history.

(56) References Cited

U.S. PATENT DOCUMENTS

| | | | |
|---|---|---|---|
| 7,010,347 B2 | 3/2006 | Schecter | |
| 7,286,871 B2 | 10/2007 | Cohen | |
| 7,528,338 B2 | 5/2009 | Ataka | |
| 8,521,266 B2 | 8/2013 | Narayan et al. | |
| 9,211,110 B2* | 12/2015 | Rubin | A61B 8/485 |
| 9,706,935 B2 | 7/2017 | Spector | |
| 10,315,144 B2 | 6/2019 | Reichter et al. | |
| 10,556,113 B2 | 2/2020 | Villongco et al. | |
| 10,856,816 B2 | 12/2020 | Villongco | |
| 2002/0035334 A1 | 1/2002 | Ooishi et al. | |
| 2004/0015081 A1 | 1/2004 | Kramer et al. | |
| 2004/0176697 A1 | 1/2004 | Li et al. | |
| 2005/0251013 A1* | 11/2005 | Krishnan | G06T 7/0012 600/407 |
| 2007/0016108 A1 | 1/2007 | Camus et al. | |
| 2007/0032733 A1 | 1/2007 | Yasuda | |
| 2007/0259031 A1 | 2/2007 | Kong et al. | |
| 2007/0270703 A1 | 2/2007 | Szeto et al. | |
| 2007/0081707 A1* | 4/2007 | Sirohey | G16Z 99/00 382/128 |
| 2007/0276214 A1* | 11/2007 | Dachille | G16H 30/40 600/407 |
| 2008/0021336 A1 | 1/2008 | Dobak | |
| 2009/0306732 A1 | 1/2009 | Chakra et al. | |
| 2010/0016917 A1 | 1/2010 | Efimov et al. | |
| 2010/0152796 A1 | 6/2010 | Schecter | |
| 2010/0280355 A1 | 11/2010 | Grimm et al. | |
| 2010/0298904 A1 | 11/2010 | Blomqvist et al. | |
| 2011/0251504 A1 | 10/2011 | Tereshchenko et al. | |
| 2011/0251505 A1 | 10/2011 | Narayan et al. | |
| 2011/0307231 A1 | 12/2011 | Kirchner et al. | |
| 2011/0311116 A1* | 12/2011 | Benn | G06T 11/00 382/128 |
| 2012/0035459 A1 | 2/2012 | Revishvili et al. | |
| 2012/0087563 A1* | 4/2012 | Ionasec | G06T 19/006 382/128 |
| 2012/0165674 A1* | 6/2012 | Abe | A61B 8/5284 600/443 |
| 2012/0283587 A1 | 11/2012 | Gosh et al. | |
| 2013/0006131 A1 | 1/2013 | Narayan et al. | |
| 2013/0034203 A1 | 2/2013 | Wang et al. | |
| 2013/0096394 A1 | 4/2013 | Gupta et al. | |
| 2013/0131529 A1 | 5/2013 | Jia et al. | |
| 2013/0158557 A1* | 6/2013 | Komistek | A61B 17/15 623/22.21 |
| 2013/0197881 A1 | 8/2013 | Mansi et al. | |
| 2013/0211256 A1 | 8/2013 | Russell et al. | |
| 2014/0005562 A1 | 1/2014 | Bunch et al. | |
| 2014/0088943 A1 | 3/2014 | Trayanova et al. | |
| 2014/0107510 A1 | 4/2014 | Bogun et al. | |
| 2014/0200575 A1 | 7/2014 | Spector | |
| 2014/0241988 A1 | 8/2014 | Jalife | |
| 2014/0276152 A1 | 9/2014 | Narayan et al. | |
| 2014/0323882 A1 | 10/2014 | Ghosh et al. | |
| 2014/0329907 A1 | 11/2014 | Ye | |
| 2015/0042646 A1 | 2/2015 | Comaniciu et al. | |
| 2015/0216432 A1 | 8/2015 | Yang | |
| 2015/0216434 A1 | 8/2015 | Ghosh et al. | |
| 2015/0216438 A1 | 8/2015 | Bokan et al. | |
| 2015/0313510 A1 | 11/2015 | Razavi et al. | |
| 2016/0005106 A1 | 1/2016 | Giraldez et al. | |
| 2016/0012592 A1 | 1/2016 | Chou et al. | |
| 2016/0022375 A1 | 1/2016 | Blake et al. | |
| 2016/0135702 A1 | 5/2016 | Perez | |
| 2016/0157769 A1 | 6/2016 | Min et al. | |
| 2016/0210435 A1* | 7/2016 | Neumann | G09B 23/288 |
| 2016/0262635 A1 | 9/2016 | McCullouch et al. | |
| 2016/0331337 A1 | 11/2016 | Ben-Haim | |
| 2017/0027649 A1 | 2/2017 | Kiraly et al. | |
| 2017/0079542 A1 | 3/2017 | Spector | |
| 2017/0178403 A1 | 6/2017 | Krummen et al. | |
| 2017/0185740 A1 | 6/2017 | Seegerer et al. | |
| 2017/0209698 A1 | 7/2017 | Villongco et al. | |
| 2017/0304005 A1* | 10/2017 | Maino | A61C 7/002 |
| 2017/0319278 A1 | 11/2017 | Trayanova et al. | |
| 2017/0367603 A1 | 12/2017 | Spector | |
| 2018/0028265 A1* | 2/2018 | Azevedo Da Silva | A61B 34/10 |
| 2018/0055401 A1 | 3/2018 | Wang et al. | |
| 2018/0318606 A1 | 11/2018 | Robinson et al. | |
| 2019/0104951 A1 | 4/2019 | Valys et al. | |
| 2019/0206127 A1 | 7/2019 | Krummen et al. | |
| 2019/0282821 A1 | 9/2019 | Masuda et al. | |
| 2019/0304183 A1 | 10/2019 | Krummen et al. | |
| 2020/0138394 A1* | 5/2020 | Vanden Berghe | G06T 17/00 |
| 2020/0349699 A1* | 11/2020 | Shah | G06T 11/008 |
| 2021/0346091 A1* | 11/2021 | Haslam | A61B 34/10 |

FOREIGN PATENT DOCUMENTS

| | | |
|---|---|---|
| WO | WO-2009079344 A1 | 6/2009 |
| WO | WO-2010042826 A1 | 4/2010 |
| WO | WO-2010052303 A1 | 5/2010 |
| WO | WO-2010054409 A1 | 5/2010 |
| WO | WO-2012055498 A1 | 5/2012 |
| WO | WO-20120109618 A2 | 8/2012 |

OTHER PUBLICATIONS

Alexander, D. C., et. al. "Spatial Transformations of Diffusion Tensor Magnetic Resonance Images." *IEEE Transactions on Medical Imaging*, vol. 20 No. 11, 2001, pp. 1131-1139.

Aronszajn, N. "Theory of reproducing kernels." *Transactions of the American Mathematical Society*, vol. 68, 1950, pp. 337-404.

Arsigny, V., et. al. "Log-Euclidean metrics for fast and simple calculus on diffusion tensors." *Magnetic Resonance in Medicine :*

(56) References Cited

OTHER PUBLICATIONS

*Official Journal of the Society of Magnetic Resonance in Medicine / Society of Magnetic Resonance in Medicine*, vol. 56 No. 2, 2006, pp. 411-21.

Auricchio, A., et. al. "Characterization of left ventricular activation in patients with heart failure and left bundle-branch block." *Circulation*, vol. 109, No. 9, 2004, pp. 1133-9.

Bazan, V., et al., "Three-dimensional myocardial scar characterization from the endocardium: Usefulness of endocardial unipolar electroanatomic mapping." J Cardiovasc Electrophysiol 2019;30:427-437.

Berger, T., et. al."Single-beat noninvasive imaging of cardiac electrophysiology of ventricular pre-excitation." *Journal of the American College of Cardiology*, vol. 48, No. 10, 2006, pp. 2045-52.

Burger, H. C., et al., "Heart-Vector and Leads." British Heart Journal, vol. 8, No. 3, 1946, pp. 157-61.

Cao, Y., et. al. "Large deformation diffeomorphic metric mapping of vector fields." *Medical Imaging, IEEE Transactions*, vol. 24, No. 9, 2005, pp. 1216-1230.

Carrault, G., et al., "A model-based approach for learning to identify cardiac arrhythmias." Joint European Conference on Artificial Intelligence in Medicine and medical Decision Making. Springer, Berlin, Heidelberg, 1999. (Year: 1999).

Carrault, G., et al., "Temporal abstraction and inductive logic programming for arrhythmia recognition from electrocardigrams." Artificial intelligence in medicine 28.3 (2003): 231-263. (Year: 2003).

Chalil, S., et al., "Intraventricular Dyssynchrony Predicts Mortality and Morbidity After Cardiac Resynchronization Therapy A Study Using Cardiovascular Magnetic Resonance Tissue Synchronization Imaging", Journal of The American College of Cardiology, vol. 50, No. 3, pp. 243-252, XP029654014, ISSN: 0735-1097, DOI: 10.1016/J.JACC. 2007.03.035.

Cluitmans, M. J. M., et. al. "Inverse Reconstruction of Epicardial Potentials Improve by Vectorcardiography and Realistic Potentials." *Computing in Cardiology*, vol. 40, 2013, pp. 369-372.

Cobb, L.A., et al., "Changing incidence of out-of-hospital ventricular fibrillation, 1980-2000." Jama 288.23 (2002): 3008-3013.

Coronel, R., et al, "Right ventricular fibrosis and conduction delay in a patient with clinical signs of Brugada syndrome: a combined electrophysiological, genetic, histopathologic, and computational study." Circulation. 2005;112:2769-77.

Cortez, D.L et al., "When deriving the spatial QRS-T angle from the 12-lead electrocardiogram, which transform is more Frank: regression or inverse Dower?" Journal of Electrocardiology 43.4 (2010): 302-309.

Daubert, J.-C., et. al. "2012 EHRA/HRS expert consensus statement on cardiac resynchronization therapy in heart failure: implant and follow-up recommendations and management." *Heart Rhythm : The Official Journal of the Heart Rhythm Society*,vol. 9 No. 9, 2012, pp. 1524-76.

De Boeck, B.W.L., et al., "Septal rebound stretch reflects the functional substrate to cardiac resynchronization therapy and predicts volumetric and neurohormonal response." Eur J Heart Fail. 2009;1 1(9):863-71, 9 pages.

De Vito, E., et. al. "Adaptive kernel methods using the balancing principle." *Foundations of Computational Mathematics*, vol. 10, No. 4, 2010, pp. 455-479.

De Vito, E., et. al. "Learning from examples as an inverse problem." *Journal of Machine Learning Research*, vol. 6, 2005, pp. 883-904.

Dossel, O., et. al. "Imaging of bioelectric sources in the heart using a cellular automaton model." *Conference Proceedings : Annual International Conference of the IEEE Engineering in Medicine and Biology Society. IEEE Engineering in Medicine and Biology Society. Conference*, 2005, pp. 1067-70.

Edenbrandt, L., et al., "Vectorcardiogram synthesized from a 12-lead ECG: superiority of the inverse Dower matrix." Journal of Electrocardiology, vol. 21, No. 4, 1988, pp. 361-7.

Engl, H., et. al. "Regularization of Inverse Problems." *Mathematics and Its Application*, vol. 375, 1996.

Epstein A.E., et al., ACC/AHA/HRS 2008 Guidelines for Device-Based Therapy of Cardiac Rhythm AbnormalitiesPractice Guideline. J Am Coll Cardiol. 2008;51:21.

Epstein A.E., et al., American College of Cardiology F, American Heart Association Task Force on Practice G and Heart Rhythm S. 2012 ACCF/AHA/HRS focused update incorporated into the ACC/AHA/HRS 2008 guidelines for device-based therapy of cardiac rhythm abnormalities: a report of the American College of Cardiology Foundation/American Heart Association Task Force on Practice Guidelines and the Heart Rhythm Society. J Am Coll Cardiol. 2013;61:e6-75.

Fillard, P., et. al., "Clinical DT-MRI estimation, smoothing, and fiber tracking with log-Euclidean metrics." IEEE Transactions on Medical Imaging, vol. 26, No. 11, 2007, pp. 1472-82.

Gersh B.J., et al., 2011 ACCF/AHA Guideline for the Diagnosis and Treatment of Hypertrophic Cardiomyopathy: a report of the American College of Cardiology Foundation/American Heart Association Task Force on Practice Guidelines. Developed in collaboration with the American Association for Thoracic Surgery, American Society of Echocardiography, American Society of Nuclear Cardiology, Heart Failure Society of America, Heart Rhythm Society, Society for Cardiovascular Angiography and Interventions, and Society of Thoracic Surgeons. Journal of the American College of Cardiology. 2011;58:e212-60.

Gold, M. R., et. al. "The relationship between ventricular electrical delay and left ventricular remodelling with cardiac resynchronization therapy." *European Heart Journal*, vol. 32, No. 20, 2011, pp. 2516-2524.

Golub, G. H., et al., "Singular Value Decomposition and Least Squares Solutions." Numerische Mathematik, vol. 14, 1970, pp. 403-420.

Gonzales, M.J., et al., "Structural contributions to fibrillatory rotors in a patient-derived computational model of the atria." EP Europace 16.suppl 4 (2014): iv3-iv10.

Gonzales, M. J., et. al. "A three-dimensional finite element model of human atrial anatomy: new methods for cubic Hermite meshes with extraordinary vertices." *Medical Image Analysis*,vol. 17 No. 5, 2013, pp. 525-37.

Greensite, F., et al., "An improved method for estimating epicardial potentials from the body surface." IEEE Transactions on Bio-Medical Engineering, vol. 45, No. 1, 1998, pp. 98-104.

Guillem, M. S., et. al. "Derivation of orthogonal leads from the 12-lead ECG. Accuracy of a single transform for the derivation of atrial and ventricular waves." *In Computers in Cardiology*, 2006, pp. 249-252.

Gulrajani, R.M., "The forward and inverse problems of electrocardiography." IEEE Engineering in Medicine and Biology Magazine 17.5 (1998): 84-101.

Haissaguerre, M., et al., "Localized Structural Alterations Underlying a Subset of Unexplained Sudden Cardiac Death." Circ Arrhythm Electrophysiol 2018;11:e006120.

Han, C., et. al. "Noninvasive reconstruction of the three-dimensional ventricular activation sequence during pacing and ventricular tachycardia in the canine heart." *American Journal of Physiology. Heart and Circulatory Physiology*, vol. 302, No. 1, 2012, pp. H244-52.

Han, C., et. al. "Noninvasive reconstruction of the three-dimensional ventricular activation sequence during pacing and ventricular tachycardia in the rabbit heart." *Conference Proceedings: Annual International Conference of the IEEE Engineering in Medicine and Biology Society*,2011, pp. 1684-7.

He, B., et. al. "Noninvasive three-dimensional activation time imaging of ventricular excitation by means of a heart-excitation model." *Physics in Medicine and Biology*, vol. 47, No. 22, 2002, pp. 4063-78.

Helm, R.H., et al., "Cardiac Dyssynchrony Analysis Using Circumferential Versus Longitudinal Strain: Implications for Assessing Cardiac Resynchronization." Circulation. 111 (2005), pp. 2760-2767, 8 pages.

(56) References Cited

OTHER PUBLICATIONS

Ho, G., et al., "Rotors exhibit greater surface ECG variation during ventricular fibrillation than focal sources due to wavebreak, secondary rotors, and meander." J Cardiovasc Electrophysiol. 2017;28:1158-1166.

Hren, R., et al., "Value of simulated body surface potential maps as templates in localizing sites of ectopic activation for radiofrequency ablation." Physiological measurement 18.4 (1997): 373-400.

Kerckhoffs, R., et al., "Ventriculardilation and electrical dyssynchrony synergistically increase regional mechanical non-uniformity but not mechanical dyssynchrony: a computational model." Circulation: Heart Failure (2010): CIRCHEARTFAILURE-109.

Kirn, Borut, et al., "Mechanical discoordination rather than dyssynchrony predicts reverse remodeling upon cardiac resynchronization." Am J Physiol Heart Circ Physiol. 295, Aug. 2008;295(2):H640-6, 7 pages.

Kimeldorf, G., et al., "Some results on Tchebycheffian spline functions." Journal of Mathematical Analysis and Applications, vol. 33, 1971, pp. 82-95.

Kindermann, S., et al., "On the convergence of the quasi-optimality criterion for (iterated) Tikhonov regularization." Inverse Problems and Imaging, vol. 2, No. 2, 2008, pp. 291-299.

Kors, J. A., et. al. "Reconstruction of the Frank vectorcardiogram from standard electrocardiographic leads: diagnostic comparison of different methods." *European Heart Journal*, vol. 11, No. 12, 1990, pp. 1083-92.

Krishnamurthy, A., et al., "CRT Response is Greater in Patients With Larger Fraction of the Myocardium Performing Negative Regional Work." Circulation 128.Suppl 22 (2013): A11135-A11135, Abstract only.

Krishnamurthy, A., et al., "Patient-specific models of cardiac biomechanics." Journal of computational physics 244 (2013): 4-21.

Krummen, D.E., et al., "Mechanisms of human atrial fibrillation initiation: clinical and computational studies of repolarization restitution and activation latency." Circ Arrhythm Electrophysiol 2012;5:1149-59.

Krummen, D.E., et al., "Modifying Ventricular Fibrillation by Targeted Rotor Substrate Ablation: Proof-of-Concept from Experimental Studies to Clinical VF." J Cardiovasc Electrophysiol 2015;26:1117-26.

Krummen, D.E., et al., "Rotor stability separates sustained ventricular fibrillation from self-terminating episodes in humans." Journal of the American College of Cardiology 63.24 (2014): 2712-2721.

Leclercq, C., et al., "Systolic Improvement and Mechanical Resynchronization Does Not Require Electrical Synchrony in the Dilated Failing Heart With Left Bundle-Branch Block." Circulation, 106 (2002). pp. 1760-1763, 4 pages.

Li, G., et al., "Localization of the site of origin of cardiac activation by means of a heart-model-based electrocardiographic imaging approach." IEEE Transactions on Bio-Medical Engineering, vol. 48, No. 6, 2001, pp. 660-9.

Lin, T., et. al. "Implant electrical characteristics predict response to cardiac resynchronization therapy." *World Journal of Cardiovascular Diseases*, 2014.

Liu, C., et. al. "Estimation of global ventricular activation sequences by noninvasive 3-dimensional electrical imaging: validation studies in a swine model during pacing." *Journal of Cardiovasc Electrophysiol*, vol. 19, No. 5, 2009, pp. 535-540.

McVeigh, E.R., et al., "Regional myocardial strain measurements from 4DCT in patients with normal LV function." J Cardiovasc Comput Tomogr 2018;12:372-378.

Messinger-Rapport, B. J., et al., "Regularization of the inverse Problem in Electrocardiography: A Model Study." Mathematical Biosciences, vol. 89, 1998, pp. 79-118.

Messnarz, B., et al., "A new spatiotemporal regularization approach for reconstruction of cardiac transmembrane potential patterns." IEEE transactions on Biomedical Engineering 51.2 (2004): 273-281.

Micchelli, C. A., et al., "Learning the kernel function via regularization." Journal of Machine Learning Research, vol. 6, 2005, pp. 1099-1125.

Myerburg R.J., et al., "Interpretation of outcomes of antiarrhythmic clinical trials: design features and population impact." Circulation. 1998;97:1514-21.

Narayan, S.M., et al., "Steep restitution of ventricular action potential duration and conduction slowing in human Brugada syndrome." Heart Rhythm. 2007;4:1087-9.

Nash, M.P., et al., "Evidence for multiple mechanisms in human ventricular fibrillation." Circulation 114.6 (2006): 536-542.

Naumova, V., et. al. "Extrapolation in variable RKHSs with application to the blood glucose reading." *Inverse Problems*, vol. 27, No. 7, 2011, pp. 1-13.

Naumova, V., et. al. "A meta-learning approach to the regularized learning—case study: Blood glucose prediction." *Neural Networks*, vol. 33, 2012, pp. 181-193.

Niederer, S.A., et al., "Analyses of the Redistribution of Work following Cardiac Resynchronisation Therapy in a Patient Specific Model." PLoS ONE 7(8), 2012, 9 pages.

O'Hanlon, R., et al., "Prognostic significance of myocardial fibrosis in hypertrophic cardiomyopathy." Journal of the American College of Cardiology. 2010;56:867-74.

Oster, H.S., et al., "Noninvasive electrocardiographic imaging: reconstruction of epicardial potentials, electrograms, and isochrones and localization of single and multiple electrocardiac events." Circulation. 1997;96:1012-24.

Oster, H. S., et al., "The use of temporal information in the regularization of the inverse problem of electrocardiography." IEEE Transactions on Bio-Medical Engineering, vol. 39, No. 1, 1992, pp. 65-75.

Pfeifer, B., et. al. "Patient-specific vol. conductor modeling for non-invasive imaging of cardiac electrophysiology." *The Open Medical Informatics Journal*, vol. 2, 2008, pp. 32-41.

Ploux, S., et. al. "Noninvasive electrocardiographic mapping to improve patient selection for cardiac resynchronization therapy: beyond QRS duration and left bundle branch block morphology." *Journal of the American College of Cardiology*, vol. 61, No. 24, 2013, pp. 2435-43.

Ramanathan, C., et. al. "Noninvasive electrocardiographic imaging for cardiac electrophysiology and arrhythmia." *Nature Medicine*, vol. 10, No. 4, 2004, pp. 422-8.

Ramanathan, C., et. al. "Noninvasive Electrocardiographic Imaging (ECGI): Application of the Generalized Minimal Residual (GMRes) Method." *Annals of Biomedical Engineering*, vol. 31, No. 8, 2003, pp. 981-994.

Rodriguez, L.-M., et. al. "Variable patterns of septal activation in patients with left bundle branch block and heart failure." *Journal of Cardiovascular Electrophysiology*, vol. 14, No. 2, 2003, pp. 135-41.

Rotter, M., et. al. "Reduction of fluoroscopy exposure and procedure duration during ablation of atrial fibrillation using a novel anatomical navigation system." *European Heart Journal*, vol. 26, No. 14, 2005, pp. 1415-1421.

Rudy, Y. "Noninvasive electrocardiographic imaging of arrhythmogenic substrates in humans." *Circulation Research*, vol. 112, No. 5, 2013, pp. 863-74.

Schreck, D. M.,et. al. "Statistical methodology: VI. Mathematical modeling of the electrocardiogram using factor analysis." *Academic Emergency Medicine*, vol. 5, No. 9, 1998, pp. 929-934.

Seo, Y., et al., "Mechanical dyssynchrony assessed by speckle tracking imaging as a reliable predictor of acute and chronic response to cardiac resynchronization therapy." Journal of the American Society of Echocardiography 22.7 (2009): 839-846.

Singh, J. P., et. al. "Left ventricular lead electrical delay predicts response to cardiac resynchronization therapy." *Heart Rhythm*, vol. 3, No. 11, 2006, pp. 1285-1292.

Stecker, E.C., et al., "Population-based analysis of sudden cardiac death with and without left ventricular systolic dysfunction: two-year findings from the Oregon Sudden Unexpected Death Study." J Am Coll Cardiol. 2006;47:1161-6.

(56) References Cited

OTHER PUBLICATIONS

Stevenson, W.G., et al., "Identification of reentry circuit sites during catheter mapping and radiofrequency ablation of ventricular tachycardia late after myocardial infarction." Circulation 1993;88:1647-70.
Strauss, D. G., et. al. "Defining left bundle branch block in the era of cardiac resynchronization therapy." *The American Journal of Cardiology*, vol. 107, No. 6, 2011, pp. 927-34.
Sweeney, M. O., et. al. "Analysis of ventricular activation using surface electrocardiography to predict left ventricular reverse volumetric remodeling during cardiac resynchronization therapy." *Circulation*, vol. 121, No. 5, 2010, pp. 626-634.
Taggart, P., et al. "Developing a novel comprehensive framework for the investigation of cellular and whole heart electrophysiology in the in situ human heart: Historical perspectives, current progress and future prospects."& nbsp;Progress in biophysics and molecular biology & nbsp;115.2-3 (2014): 252-260.
Ten Tusscher, K.H.W.J., et al., "Alternans and spiral breakup in a human ventricular tissue model. American Journal of Physiology." Heart and Circulatory Physiology, vol. 291,2006, pp. H1088-H1100.
Ten Tusscher, K. H. W. J., et al., "A model for human ventricular tissue." American Journal of Physiology—Heart and Circulatory Physiology 286.4 (2004): H1573-H1589.
Tikhonov, A. N., et al. Solutions of ill-posed problems. Winston, (p. 258), 1997.
Tikhonov, A. N., et al., "Use of the regularization methods in non-linear problems." USSR Computational Mathematics and Mathematical Physics, vol. 5, 1965.
Tobon, C., et al., "Dominant frequency and organization index maps in a realistic three-dimensional computational model of atrial fibrillation."& nbsp;Europace & nbsp;14.suppl 5 (2012): v25-v32.
Vadakkumpadan, F., et. al. "Image-based estimation of ventricular fiber orientations for personalized modeling of cardiac electrophysiology." *Medical Imaging, IEEE Transactions*, vol. 31, No. 5, 2012, pp. 1051-1060.
Van der Graaf, A. W. M., et. al. "Noninvasive imaging of cardiac excitation: current status and future perspective. Annals of Noninvasive Electrocardiology." *The Official Journal of the International Society for Holter and Noninvasive Electrocardiology, Inc*, vol. 19, No. 2, 2014, pp. 105-13.
Van Deursen, C. J., et. al. "Vectorcardiography as a tool for easy optimization of cardiac resynchronization therapy in canine left bundle branch block hearts." *Circulation: Arrhythmia and Electrophysiology*, vol. 5, No. 3, 2012, pp. 544-552.
Vaquero, M., et. al. "Cardiac Fibrillation: From Ion Channels to Rotors in the Human Heart." *Heart Rhythm : The Official Journal of the Heart Rhythm Society*, vol. 5, No. 6, 2008, pp. 872-879.
Varma, N., et. al. "Electrocardiographic imaging of patients with heart failure with left bundle branch block and response to cardiac resynchronization therapy." *Journal of Electrocardiology*, vol. 40,2007, pp. S174-8.
Villongco, C. T., et. al. "Patient-specific modeling of ventricular activation pattern using surface ecg-derived vectorcardiogram in bundle branch block." *Progress in Biophysics and Molecular Biology*, vol. 115, No. 2, 2014, pp. 305-313.
Wang, Y., et. al. "Noninvasive electroanatomic mapping of human ventricular arrhythmias with electrocardiographic imaging." *Science Translational Medicine*, vol. 3, No. 98, 2011, p. 98ra84.
Wittkampf, F. H., et. al. "LocaLisa new technique for real-time 3-dimensional localization of regular intracardiac electrodes." *Circulation*, vol. 99, No. 10, 1999, pp. 1312-1317.
Yamashita, Y. "Theoretical studies on the inverse problem in electrocardiography and the uniqueness of the solution." *Biomedical Engineering, IEEE Transactions*, vol. 11, 1982, pp. 719-725.
Yokokawa, M. et al., "Automated analysis of the 12-lead electrocardiogram to identify the exit site of prostinfarction ventricular tachycardia." Heart Rhythm Society vol. 9, No. 3, Mar. 2012: 330-334, (5 pages).
Yushkevich, P. A., et. al. "User-guided 3D active contour segmentation of anatomical structures: significantly improved efficiency and reliability." *NeuroImage*, vol. 31, No. 3, 2006, pp. 1116-28.
Zhang, J., et al., "Cardiac electrophysiological substrate underlying the ECG phenotype and electrogram abnormalities in Brugada syndrome patients." Circulation. 2015;131:1950-9.
Zhang, X., et. al. "Noninvasive three-dimensional electrocardiographic imaging of ventricular activation sequence." *AJP-Heart Circulatory Physiology*, vol. 289, 2005, pp. 2724-2732.
Man, S.-C. et al., "Reconstruction of standard 12-lead electrocardiograms from 12-lead electrocardiograms recorded with the Mason-Likar electrode configuration," Journal of Electrocardiology, vol. 14 (2008), pp. 211-219.
Extended European Search Report issued in European Application No. 19831553.3-1113, dated Mar. 3, 2022, 9 pages.

\* cited by examiner

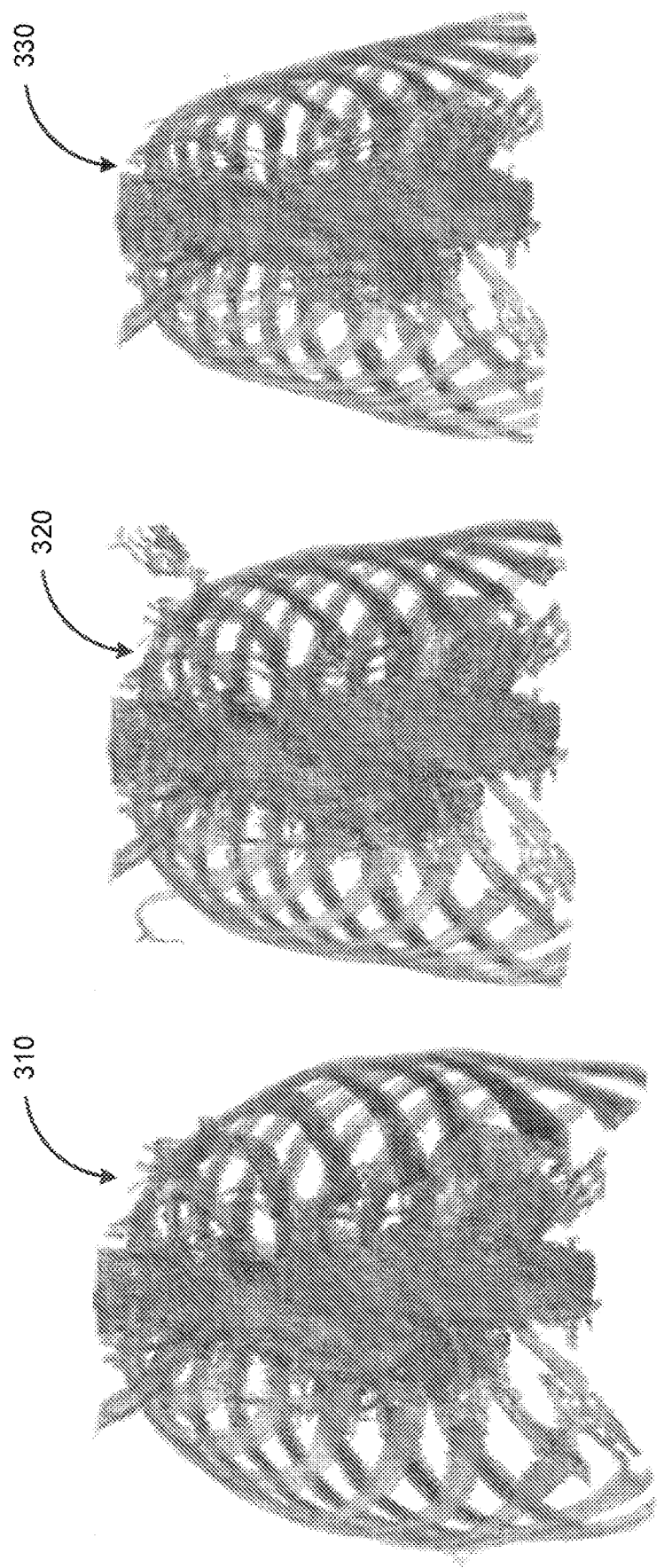

COMPUTATIONAL SIMULATIONS OF ANATOMICAL STRUCTURES AND BODY SURFACE ELECTRODE POSITIONING

This Application is a Continuation of Application PCT/US19/40740 filed on Jul. 5, 2019. Application PCT/US19/40740 claims the benefit of U.S. Provisional Application 62/694,401 filed on Jul. 5, 2018. The entire contents of these applications are incorporated herein by reference in their entirety.

RELATED APPLICATION

This application claims priority to U.S. Provisional Application No. 62/694,401 entitled "COMPUTATIONAL THORACIC AND ECG TRANSFORM VIA 2D RADIOGRAPHY" and filed on Jul. 5, 2018, the disclosure of which is incorporated herein by reference in its entirety.

TECHNICAL FIELD

The subject matter described herein relates generally to medical imaging and more specifically to computationally simulating images of anatomical structures and electrical activity to permit the accurate determination of subject 3-dimensional anatomy and electrical rhythm diagnosis and source localization.

BACKGROUND

Medical imaging refers to techniques and processes for obtaining data characterizing a subject's internal anatomy and pathophysiology including, for example, images created by the detection of radiation either passing through the body (e.g. x-rays) or emitted by administered radiopharmaceuticals (e.g. gamma rays from technetium (99 mTc) medronic acid given intravenously). By revealing internal anatomical structures obscured by other tissues such as skin, subcutaneous fat, and bones, medical imagining is integral to numerous medical diagnosis and/or treatments. Examples of medical imaging modalities include 2-dimensional imaging such as: x-ray plain films; bone scintigraphy; and thermography, and 3-dimensional imaging modalities such as: magnetic resonance imaging (MRI); computed tomography (CT), cardiac sestamibi scanning, and positron emission tomography (PET) scanning.

SUMMARY

Systems, methods, and articles of manufacture, including computer program products, are provided for computationally simulating a three-dimensional representation of an anatomical structure. In some example embodiments, there is provided a system that includes at least one processor and at least one memory. The at least one memory may include program code that provides operations when executed by the at least one processor. The operations may include: identifying, in a library including a plurality of simulated three-dimensional representations, a first simulated three-dimensional representation corresponding to a first internal anatomy of a first subject, the first simulated three-dimensional representation being identified based at least on a match between a first computed two-dimensional image corresponding to the first simulated three-dimensional representation and a two-dimensional image depicting the first internal anatomy of the first subject; and generating an output including the simulated three-dimensional representation of the first internal anatomy of the first subject.

In some variations, one or more features disclosed herein including the following features can optionally be included in any feasible combination. The operations may further include generating the library including by generating, based on a first three-dimensional representation of a second internal anatomy of a second subject, the first simulated three-dimensional representation. The first simulated three-dimensional representation may be generated by at least varying one or more attributes of the second internal anatomy of the second subject. The one or more attributes may include a skeletal property, an organ geometry, a musculature, and/or a subcutaneous fat distribution. The library may be further generated to include the first three-dimensional representation of the second internal anatomy of the second subject and/or a second three-dimensional representation of a third internal anatomy of a third subject having at least one different attribute than the second internal anatomy of the second subject.

In some variations, the generating of the library may include generating, based at least on the first simulated three-dimensional representation, the first computed two-dimensional image. The generating of the first computed two-dimensional image may include determining, based at least on a density and/or a transmissivity of one or more tissues included in the first simulated three-dimensional representation, a quantity of radiation able to pass through the one or more tissues included in the first simulated three-dimensional representation to form the first computed two-dimensional image.

In some variations, the first three-dimensional representation of the second internal anatomy of the second subject may include a computed tomography (CT) scan and/or a magnetic resonance imaging (MRI) scan depicting the second internal anatomy of the second subject.

In some variations, the first simulated three-dimensional representation may be further associated with a diagnosis of a condition depicted in the first simulated three-dimensional representation, and wherein the output is further generated to include the diagnosis.

In some variations, the operations may further include determining a first similarity index indicating a closeness of the match between the first computed two-dimensional image and the two-dimensional image depicting the first internal anatomy of the first subject. The first simulated three-dimensional representation may be identified as corresponding to the first internal anatomy of the first subject based at least on the first similarity index exceeding a threshold value and/or the first similarity index being greater than a second similarity index indicating a closeness of a match between a second computed two-dimensional image corresponding to a second simulated three-dimensional representation and the two-dimensional image depicting the first internal anatomy of the first subject.

In some variations, the first computed two-dimensional image may be determined to match the two-dimensional image depicting the first internal anatomy of the first subject by at least applying an image comparison technique. The image comparison technique may include scale invariant feature transform (SIFT), speed up robust feature (SURF), binary robust independent elementary features (BRIEF), and/or oriented FAST and rotated BRIEF (ORB).

In some variations, the image comparison technique may include a machine learning model. The machine learning model may include an autoencoder and/or a neural network.

In some variations, the operations may further include: determining, based at least on the two-dimensional image depicting the first internal anatomy of the first subject, a lead placement for a recording device configured to measure an electrical activity of an organ, the recording device including one or more leads configured to detect a change in voltage on a body surface corresponding to the electrical activity of the organ; and generating, based at least on the lead placement and the first simulated three-dimensional representation of the first internal anatomy of the first subject, a simulation of the electrical activity measured by the recording device.

In some variations, the simulation of the electrical activity measured by the recording device may include a signal detected by each of the one or more leads included in the recording device. The recording device may be configured to perform an electrocardiography (ECG) and/or an electroencephalography (EEG). The output may be further generated to include the lead placement and/or the simulation of the electrical activity measured by the recording device.

In some variations, the identifying of the first simulated three-dimensional representation may further include eliminating a second simulated three-dimensional representation based at least on a mismatch between a demographics and/or a vital statistics of the first subject and a second subject depicted in the second simulated three-dimensional representation.

In some variations, the identifying of the first simulated three-dimensional representation may further include eliminating a second simulated three-dimensional representation based at least on a condition depicted in the second simulated three-dimensional representation being inconsistent with one or more symptoms of the first subject.

In some variations, the operations may further include providing, to a client, the output including by sending, to the client, at least a portion of the output and/or generating a user interface configured to display at least the portion of the output at the client.

In another aspect, there is provided a method for computationally simulating a three-dimensional representation of an anatomical structure. The method may include: identifying, in a library including a plurality of simulated three-dimensional representations, a first simulated three-dimensional representation corresponding to a first internal anatomy of a first subject, the first simulated three-dimensional representation being identified based at least on a match between a first computed two-dimensional image corresponding to the first simulated three-dimensional representation and a two-dimensional image depicting the first internal anatomy of the first subject; and generating an output including the simulated three-dimensional representation of the first internal anatomy of the first subject.

In some variations, one or more features disclosed herein including the following features can optionally be included in any feasible combination. The method may further include generating the library including by generating, based on a first three-dimensional representation of a second internal anatomy of a second subject, the first simulated three-dimensional representation. The first simulated three-dimensional representation may be generated by at least varying one or more attributes of the second internal anatomy of the second subject. The one or more attributes may include a skeletal property, an organ geometry, a musculature, and/or a subcutaneous fat distribution. The library may be further generated to include the first three-dimensional representation of the second internal anatomy of the second subject and/or a second three-dimensional representation of a third internal anatomy of a third subject having at least one different attribute than the second internal anatomy of the second subject.

In some variations, the generating of the library may include generating, based at least on the first simulated three-dimensional representation, the first computed two-dimensional image. The generating of the first computed two-dimensional image may include determining, based at least on a density and/or a transmissivity of one or more tissues included in the first simulated three-dimensional representation, a quantity of radiation able to pass through the one or more tissues included in the first simulated three-dimensional representation to form the first computed two-dimensional image.

In some variations, the first three-dimensional representation of the second internal anatomy of the second subject may include a computed tomography (CT) scan and/or a magnetic resonance imaging (MRI) scan depicting the second internal anatomy of the second subject.

In some variations, the first simulated three-dimensional representation may be further associated with a diagnosis of a condition depicted in the first simulated three-dimensional representation, and wherein the output is further generated to include the diagnosis.

In some variations, the method may further include determining a first similarity index indicating a closeness of the match between the first computed two-dimensional image and the two-dimensional image depicting the first internal anatomy of the first subject. The first simulated three-dimensional representation may be identified as corresponding to the first internal anatomy of the first subject based at least on the first similarity index exceeding a threshold value and/or the first similarity index being greater than a second similarity index indicating a closeness of a match between a second computed two-dimensional image corresponding to a second simulated three-dimensional representation and the two-dimensional image depicting the first internal anatomy of the first subject.

In some variations, the first computed two-dimensional image may be determined to match the two-dimensional image depicting the first internal anatomy of the first subject by at least applying an image comparison technique. The image comparison technique may include scale invariant feature transform (SIFT), speed up robust feature (SURF), binary robust independent elementary features (BRIEF), and/or oriented FAST and rotated BRIEF (ORB).

In some variations, the image comparison technique may include a machine learning model. The machine learning model may include an autoencoder and/or a neural network.

In some variations, the method may further include: determining, based at least on the two-dimensional image depicting the first internal anatomy of the first subject, a lead placement for a recording device configured to measure an electrical activity of an organ, the recording device including one or more leads configured to detect a change in voltage on a body surface corresponding to the electrical activity of the organ; and generating, based at least on the lead placement and the first simulated three-dimensional representation of the first internal anatomy of the first subject, a simulation of the electrical activity measured by the recording device.

In some variations, the simulation of the electrical activity measured by the recording device may include a signal detected by each of the one or more leads included in the recording device. The recording device may be configured to perform an electrocardiography (ECG) and/or an electroencephalography (EEG). The output may be further generated to include the lead placement and/or the simulation of the electrical activity measured by the recording device.

In some variations, the identifying of the first simulated three-dimensional representation may further include eliminating a second simulated three-dimensional representation based at least on a mismatch between a demographics and/or a vital statistics of the first subject and a second subject depicted in the second simulated three-dimensional representation.

In some variations, the identifying of the first simulated three-dimensional representation may further include eliminating a second simulated three-dimensional representation based at least on a condition depicted in the second simulated three-dimensional representation being inconsistent with one or more symptoms of the first subject.

In some variations, the method may further include providing, to a client, the output including by sending, to the client, at least a portion of the output and/or generating a user interface configured to display at least the portion of the output at the client.

In another aspect, there is provided a computer program product including a non-transitory computer readable medium storing instructions. The instructions may cause operations may executed by at least one data processor. The operations may include: identifying, in a library including a plurality of simulated three-dimensional representations, a first simulated three-dimensional representation corresponding to a first internal anatomy of a first subject, the first simulated three-dimensional representation being identified based at least on a match between a first computed two-dimensional image corresponding to the first simulated three-dimensional representation and a two-dimensional image depicting the first internal anatomy of the first subject; and generating an output including the simulated three-dimensional representation of the first internal anatomy of the first subject.

In another aspect, there is provide an apparatus for computationally simulating a three-dimensional representation of an anatomical structure. The apparatus may include: means for identifying, in a library including a plurality of simulated three-dimensional representations, a first simulated three-dimensional representation corresponding to a first internal anatomy of a first subject, the first simulated three-dimensional representation being identified based at least on a match between a first computed two-dimensional image corresponding to the first simulated three-dimensional representation and a two-dimensional image depicting the first internal anatomy of the first subject; and means for generating an output including the simulated three-dimensional representation of the first internal anatomy of the first subject.

Systems, methods, and articles of manufacture, including computer program products, are also provided for computationally correcting a electrogram. In some example embodiments, there is provided a system that includes at least one processor and at least one memory. The at least one memory may include program code that provides operations when executed by the at least one processor. The operations may include: identifying a three-dimensional representation of at least a portion of an anatomy of a subject including a target organ; identifying a non-standard lead placement of one or more electrogram leads on a body of the subject; generating, based at least on the three-dimensional representation, one or more simulated electrical activations of the target organ; generating, based at least on the one or more simulated electrical activations, a non-standard electrogram associated with the non-standard lead placement of the one or more electrogram leads on the body of the subject; generating, based at least on the one or more simulated electrical activations, a standard electrogram associated with a standard lead placement of the one or more electrogram leads on the body of the subject; and correcting, based at least on a difference between the nonstandard electrogram and the standard electrogram, an actual electrogram generated for the subject using the non-standard lead placement.

In some variations, one or more features disclosed herein including the following features can optionally be included in any feasible combination. The standard electrogram, the nonstandard electrogram, and the actual electrogram may include electrocardiograms, electroencephalograms, or vectorcardiograms.

In some variations, the correcting may include generating a transformation matrix to transform the nonstandard electrogram to the standard electrogram and applying the transformation matrix to the actual electrogram.

In some variations, the identifying of the three-dimensional representation may include comparing a two-dimensional image of the portion of the anatomy of the subject to one or more two-dimensional images included in a library mapping the one or more two-dimensional images to one or more corresponding three-dimensional representations.

In some variations, the nonstandard lead placement may be identified based at least on an analysis of a two-dimensional image of the portion of the anatomy.

In some variations, the operations may further include identifying a simulated electrogram matching the corrected electrogram by at least searching a library including a plurality of simulated electrograms. The library may map the plurality of simulated electrograms to one or more characteristics of the target organ used to generate the plurality of simulated electrograms.

In another aspect, there is provided a method for computationally correcting an electrogram. The method may include: identifying a three-dimensional representation of at least a portion of an anatomy of a subject including a target organ; identifying a non-standard lead placement of one or more electrogram leads on a body of the subject; generating, based at least on the three-dimensional representation, one or more simulated electrical activations of the target organ; generating, based at least on the one or more simulated electrical activations, a non-standard electrogram associated with the non-standard lead placement of the one or more electrogram leads on the body of the subject; generating, based at least on the one or more simulated electrical activations, a standard electrogram associated with a standard lead placement of the one or more electrogram leads on the body of the subject; and correcting, based at least on a difference between the nonstandard electrogram and the standard electrogram, an actual electrogram generated for the subject using the non-standard lead placement.

In some variations, one or more features disclosed herein including the following features can optionally be included in any feasible combination. The standard electrogram, the nonstandard electrogram, and the actual electrogram may include electrocardiograms, electroencephalograms, or vectorcardiograms.

In some variations, the correcting may include generating a transformation matrix to transform the nonstandard electrogram to the standard electrogram and applying the transformation matrix to the actual electrogram.

In some variations, the identifying of the three-dimensional representation may include comparing a two-dimensional image of the portion of the anatomy of the subject to one or more two-dimensional images included in a library mapping the one or more two-dimensional images to one or more corresponding three-dimensional representations.

In some variations, the nonstandard lead placement may be identified based at least on an analysis of a two-dimensional image of the portion of the anatomy.

In some variations, the method may further include identifying a simulated electrogram matching the corrected electrogram by at least searching a library including a plurality of simulated electrograms. The library may map the plurality of simulated electrograms to one or more characteristics of the target organ used to generate the plurality of simulated electrograms.

In another aspect, there is provided a computer program product including a non-transitory computer readable medium storing instructions. The instructions may cause operations may executed by at least one data processor. The operations may include: identifying a three-dimensional representation of at least a portion of an anatomy of a subject including a target organ; identifying a non-standard lead placement of one or more electrogram leads on a body of the subject; generating, based at least on the three-dimensional representation, one or more simulated electrical activations of the target organ; generating, based at least on the one or more simulated electrical activations, a non-standard electrogram associated with the non-standard lead placement of the one or more electrogram leads on the body of the subject; generating, based at least on the one or more simulated electrical activations, a standard electrogram associated with a standard lead placement of the one or more electrogram leads on the body of the subject; and correcting, based at least on a difference between the nonstandard electrogram and the standard electrogram, an actual electrogram generated for the subject using the non-standard lead placement.

In another aspect, there is provided an apparatus for computationally correcting an electrogram. The apparatus may include: means for identifying a three-dimensional representation of at least a portion of an anatomy of a subject including a target organ; means for identifying a non-standard lead placement of one or more electrogram leads on a body of the subject; means for generating, based at least on the three-dimensional representation, one or more simulated electrical activations of the target organ; means for generating, based at least on the one or more simulated electrical activations, a non-standard electrogram associated with the non-standard lead placement of the one or more electrogram leads on the body of the subject; means for generating, based at least on the one or more simulated electrical activations, a standard electrogram associated with a standard lead placement of the one or more electrogram leads on the body of the subject; and means for correcting, based at least on a difference between the nonstandard electrogram and the standard electrogram, an actual electrogram generated for the subject using the non-standard lead placement.

Implementations of the current subject matter can include systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connection including, for example, a connection over a network (e.g. the Internet, a wireless wide area network, a local area network, a wide area network, a wired network, or the like), a direct connection between one or more of the multiple computing systems, and/or the like.

The details of one or more variations of the subject matter described herein are set forth in the accompanying drawings and the description below. Other features and advantages of the subject matter described herein may be apparent from the description and drawings, and from the claims. While certain features of the currently disclosed subject matter are described for illustrative purposes in relation to computationally simulating images of anatomical structures, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 3A depicts an example of a simulated three-dimensional representation of a skeletal anatomy of a reference subject, in accordance with some example embodiments;

FIG. 3B depicts another example of a simulated three-dimensional representation of a skeletal anatomy of a reference subject, in accordance with some example embodiments;

FIG. 3C depicts another example of a simulated three-dimensional representation of a skeletal anatomy of a reference subject, in accordance with some example embodiments;

When practical, similar reference numbers denote similar structures, features, or elements.

DETAILED DESCRIPTION

Figure 1:
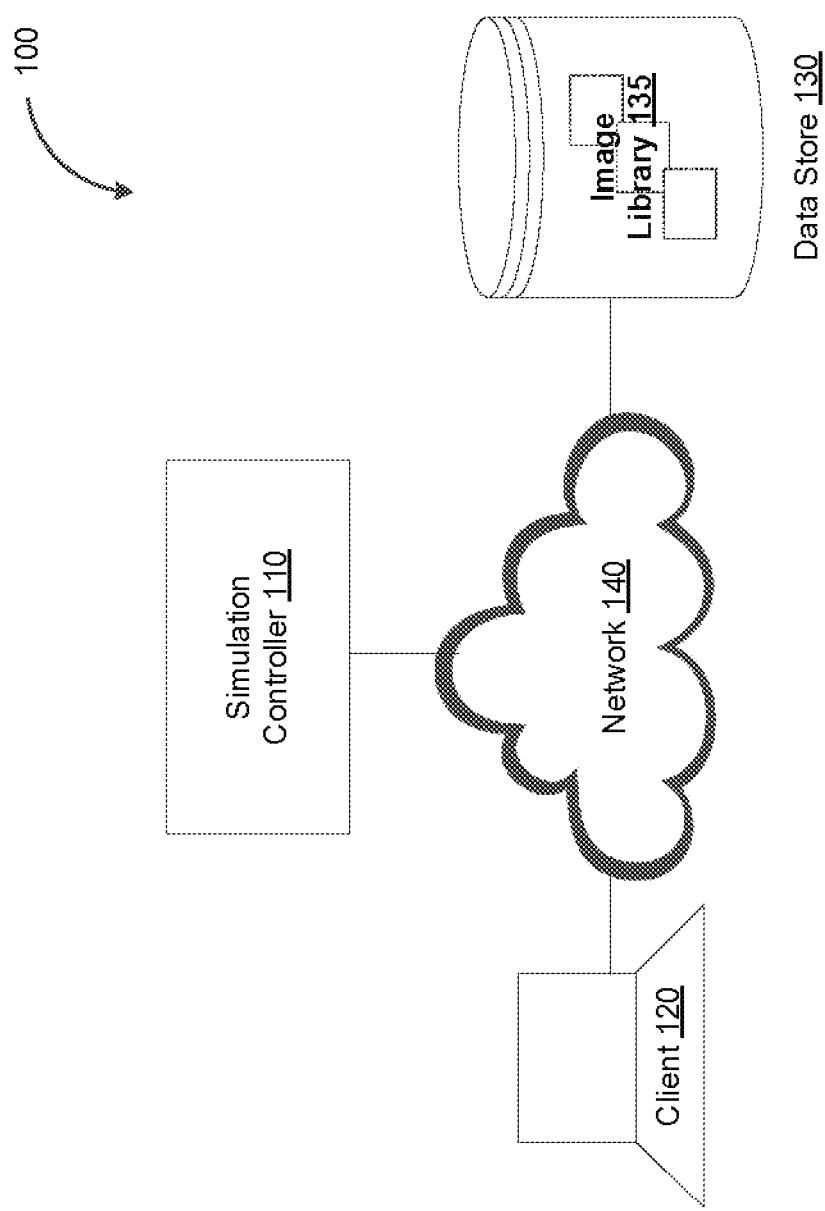
FIG. 1 depicts a system diagram illustrating an imaging system, in accordance with some example embodiments.

Although widely available and less expensive, projectional, or 2-dimensional, radiography techniques (e.g., X-ray plain films, gamma ray imaging (e.g. bone scintigraphy), fluoroscopy, and/or the like) are only able to generate two-dimensional images of a subject's internal anatomy, which may be inadequate for a variety of medical diagnosis and treatments. Conventional techniques for generating a three-dimensional representation of a subject's internal anatomy include computed tomography (CT) and magnetic resonance imaging (MRI). However, computed tomography and magnetic resonance imaging requires specialized equipment, trained technicians, often involves more time to obtain, and may be difficult to perform during invasive procedures or on critically ill subjects. As such, computed tomography and magnetic resonance imaging tend to be less accessible, more cost prohibitive, and often infeasible compared with projectional radiographs.

In some example embodiments, instead of relying on computed tomography or magnetic resonance imaging to obtain a three-dimensional representation of subject's internal anatomy, a simulated three-dimensional representation of a subject's internal anatomy may be determined based on one or more two-dimensional images of the subject's internal anatomy. For example, a simulated three-dimensional representation corresponding to the subject's internal anatomy may be identified based on one or more two-dimensional images of the subject's internal anatomy (e.g. FIGS. 6A and 6B). The two-dimensional images of the subject's internal anatomy may be obtained using a projectional radiography technique including, for example, X-rays, gamma ray imaging (e.g. bone scintigraphy), fluoroscopy, and/or the like. Meanwhile, the simulated three-dimensional representation may be part of a library of simulated three-dimensional representations, each of which being associated with one or more corresponding two-dimensional images. For instance, one or more simulated radiograph images (e.g., X-ray images, gamma ray images, and/or the like) may be generated based on each of the simulated three-dimensional representations included in the library. Accordingly, identifying the simulated three-dimensional representation corresponding to the subject's internal anatomy may include matching the two-dimensional images of the subject's internal anatomy to the computed two-dimensional images associated with the simulated three-dimensional representation.

The library of simulated three-dimensional representations includes one or more existing three-dimensional representations of the internal anatomies of one or more reference subjects including, for example, computed tomography scans, magnetic resonance imaging scans, and/or the like. The reference subjects may exhibit a variety of different anatomical attributes including, for example, variations in skeletal properties (e.g., size, abnormalities, and/or the like), organ geometry (e.g., size, relative position, and/or the like), musculature, subcutaneous fat distribution, and/or the like. As such, the simulated three-dimensional representations included in the library may also depict a variety of different anatomical attributes. Furthermore, additional anatomical variations may be introduced into the library of simulated three-dimensional representations by at least generating, based on the existing three-dimensional representations, one or more simulated three-dimensional representations that include at least variation to the internal anatomy of the corresponding reference subject. For example, in one representation, a muscle (e.g. the pectoralis major muscle) may be 5 mm in thickness. In another representation, the muscle (e.g. the pectoralis major muscle) may be 10 mm in thickness. For instance, based on an existing three-dimensional representation of the internal anatomy of a reference subject, one or more additional simulated three-dimensional representations may be generated to include variations in the skeletal properties (e.g., size, abnormalities, and/or the like), organ geometries (e.g., size, relative position, and/or the like), musculature, and/or subcutaneous fat distribution of the same reference subject.

Each simulated three-dimensional representation included in the library may be associated with one or more computed two-dimensional images including, for example, X-ray images, gamma ray images, and/or the like. A computed two-dimensional image may be generated based at least on either (a) a density and/or radiation transmissivity of the different tissues forming each of the anatomical structures (e.g., organs) included in a corresponding simulated three-dimensional representation, or (b) the absorption rate of radiopharmaceuticals (e.g. technetium (99 mTc) medronic acid and/or the like) by different tissues and the emission rate of the radiopharmaceutical. Moreover, multiple computed two-dimensional image may be generated for each simulated three-dimensional representation in order to capture different views of the simulated three-dimensional representation including, for example, a left anterior oblique view, a right anterior oblique view, a straight anterior-posterior view, and/or the like. For example, a simulated X-ray image of the simulated three-dimensional representation of a human torso may be generated based at least in part on the respective of density and/or radiation transmissivity of the various anatomical structures included in the human torso such as skin, bones, subcutaneous fat, visceral fat, heart, lungs, liver, stomach, intestines, and/or the like. In some variations, this may be accomplished using the software platform Blender (Blender Foundation, Amsterdam, Netherlands). In some variations, a 3-dimensional model of the body may be loaded into Blender. Different tissues within the model may be assigned different light transmissivities (e.g. greater transmissivity for subcutaneous fat, less transmissivity for bone). A simulated light source may be placed on one side of the model, and a flat surface placed on the other side of the model. The transmission of light through the model is computed, and an image of the projection on the two dimensional surface is recorded. This image may be further manipulated (e.g. white-black inversion) to produce a simulated 2-dimensional radiograph. As noted, in some example embodiments, the simulated three-dimensional representation corresponding to the subject's internal anatomy may be identified by least matching the two-dimensional images of the subject's internal anatomy to computed two-dimensional images associated with the simulated three-dimensional representation.

In some example embodiments, each of the simulated three-dimensional representation and the corresponding computed two-dimensional images included in the library may be associated with a diagnosis. As such, when the two-dimensional images (e.g., X-ray images, gamma ray images, and/or the like) of the subject is matched to computed two-dimensional images associated with a three-dimensional representation included in the library, a diagnosis for the subject may be determined based on the diagnosis that is associated with the computed two-dimensional images. For example, the subject may be determined to have dilated cardiomyopathy if the two-dimensional images of the subject is matched to the computed two-dimensional images associated with dilated cardiomyopathy. It should be appreciated that a two-dimensional image of the subject may be matched to one or more computed two-dimensional images by applying a variety of image comparison techniques including, for example, scale invariant feature transform (SIFT), speed up robust feature (SURF), binary robust independent elementary features (BRIEF), oriented FAST and rotated BRIEF (ORB), and/or the like. A match between a two-dimensional image of the subject and one or more computed two-dimensional images may further be determined by applying one or more machine learning-based image comparison techniques including, for example, autoencoders, neural networks, and/or the like.

For example, the match between the two-dimensional image and the one or more computed two-dimensional images may be determined by applying one or more convolutional neural networks, recurrent neural networks, and/or the like. The neural network may be trained based on training data that includes pairs of matching and/or non-matching two-dimensional images. Moreover, the neural network may be trained to examine features present in corresponding portions of the two-dimensional image of the subject and at least some of the computed two-dimensional images included in the library to determine a similarity metric between each pair of two-dimensional images.

In some example embodiments, the match between a two-dimensional image of the subject's internal anatomy and one or more computed two-dimensional images may be probabilistic. For example, when a two-dimensional image of the subject is matched to computed two-dimensional images, each of the computed two-dimensional images may be associated with a value (e.g., a similarity index and/or the like) indicating a closeness of the match between the two-dimensional image and the computed two-dimensional image. Moreover, multiple diagnosis, including a likelihood for each of the diagnosis, may be determined for the subject based on the diagnosis associated with each of the computed two-dimensional images. For instance, the diagnosis for the subject may include a first probability (e.g., an x-percentage likelihood) of the subject having dilated cardiomyopathy and a second probability (e.g., an x-percentage likelihood) of the subject having a pulmonary embolism based at least on the probabilistic match between the two-dimensional images of the subject and the computed two-dimensional images included in the library.

The electrical activities of an organ are typically measured by recording device having one more leads (e.g., pairs of electrodes measuring voltage changes), which may be placed on a surface of the body near the organ as in the case of electrocardiography (ECG) for measuring the electrical activities of the heart and electroencephalography (EEG) for measuring the electrical activities of the brain. Although a common diagnostic modality in medicine, surface recordings are associated with a number of limitations. For example, surface recordings (e.g., electrocardiography, electroencephalography, and/or the like) are performed under the assumption of a standard surface electrogram setup (e.g., lead placement) even though variations in actual lead position can alter the morphology of the resulting electrogram and/or vectorgram (e.g., electrocardiogram, electroencephalogram, vectorcardiogram, and/or the like). The morphology of the resulting electrogram can also be altered due to significant variations in individual anatomy (e.g. obesity and/or the like) and/or the presence of co-morbidities (e.g. the lung disease emphysema and/or the like), which vary the conduction of electrical signals through the body. These electrical alterations can introduce error into the diagnoses made based on the electrogram as well as the processes utilizing the electrical signals to map the organ's electrical activity (e.g. mapping the source of a cardiac arrhythmia and/or the like). As such, in some example embodiments, a subject-specific computational simulation environment that captures individual variations in body surface lead placement and subject anatomy may enable a more accurate calculation of the electrical activity of the organ (e.g. heart, brain, and/or the like). For instance, a customized computational simulation environment for a subject may be generated to include a three-dimensional representation of the internal anatomy (e.g. thoracic anatomy including the heart for measuring cardiac electrical activity) as described above. The electrical activities of an organ may be simulated based on the three-dimensional representation of the subject's internal anatomy. The simulated electrical activities may include normal electrical activations (e.g. sinus rhythm for the heart) as well as abnormal electrical activations (e.g. ventricular tachycardia). Moreover, one or more electrical properties of the organ may be determined based on the simulation of the electrical activities of the organ.

In some example embodiments, the placement of each lead of a recording device may be determined based on one or more two-dimensional images of the subject's internal anatomy. Based on the simulated electrical activities of the organ and the known locations for the leads on the surface of the subject's body, an output for the simulated recording device (e.g., the electrical signals that are detected at each electrogram lead) may be determined based on the corresponding simulated three-dimensional representation of the subject's internal anatomy to generate a simulated electrogram (e.g. a simulated electrocardiogram, a simulated electroencephalogram, and/or the like). Once the relationship between the simulated organ (e.g. heart) and simulated electrogram properties (e.g. nonstandard electrocardiogram lead positions) is determined, the relationship between each lead and the likely electrical activation pattern of the organ can be more accurately calculated. For example, the relationship between the simulated organ and the simulated electrogram properties may enable the generation of a subject-specific transformation matrix, or correction matrix, that accounts for variations in lead placement and subject anatomy. In some embodiments, the accuracy of the simulation algorithm applied to generate the simulated output may be improved by at least updating the simulation algorithm based on clinical data including actual measurements of the electrical activities of the subject's organ as measured from the body surface electrodes.

FIG. 1 depicts a system diagram illustrating an imaging system 100, in accordance with some example embodiments. Referring to FIG. 1, the imaging system 100 may include a simulation controller 110, a client 120, and a data store 130 storing an image library 135. As shown in FIG. 1, the simulation controller 110, the client 120, and the data store 130 may be communicatively coupled via a network 140. The network 140 may be a wired and/or wireless network including, for example, a wide area network (WAN), a local area network (LAN), a virtual local area network (VLAN), a public land mobile network (PLMN), the Internet, and/or the like. Meanwhile, the data store 130 may be a database including, for example, a graph database, an in-memory database, a relational database, a non-SQL (NoSQL) database, and/or the like.

In some example embodiments, the simulation controller 110 may be configured to identify, based at least on one or more two-dimensional images of the subject's internal anatomy, a simulated three-dimensional representation in the image library 135 that corresponds to the subject's internal anatomy. For example, the simulation controller 110 may receive, from the client 120, on or more two-dimensional images of the subject's internal anatomy, which may be generated using a projectional radiography technique including, for example, X-rays, gamma rays, fluoroscopy, thermography, and/or the like. The simulation controller 110 may identify the simulated three-dimensional representation as corresponding to the subject's internal anatomy based at least on the two-dimensional images of the subject's internal anatomy being matched with the computed two-dimensional images associated with the simulated three-dimensional representation.

Figure 2:
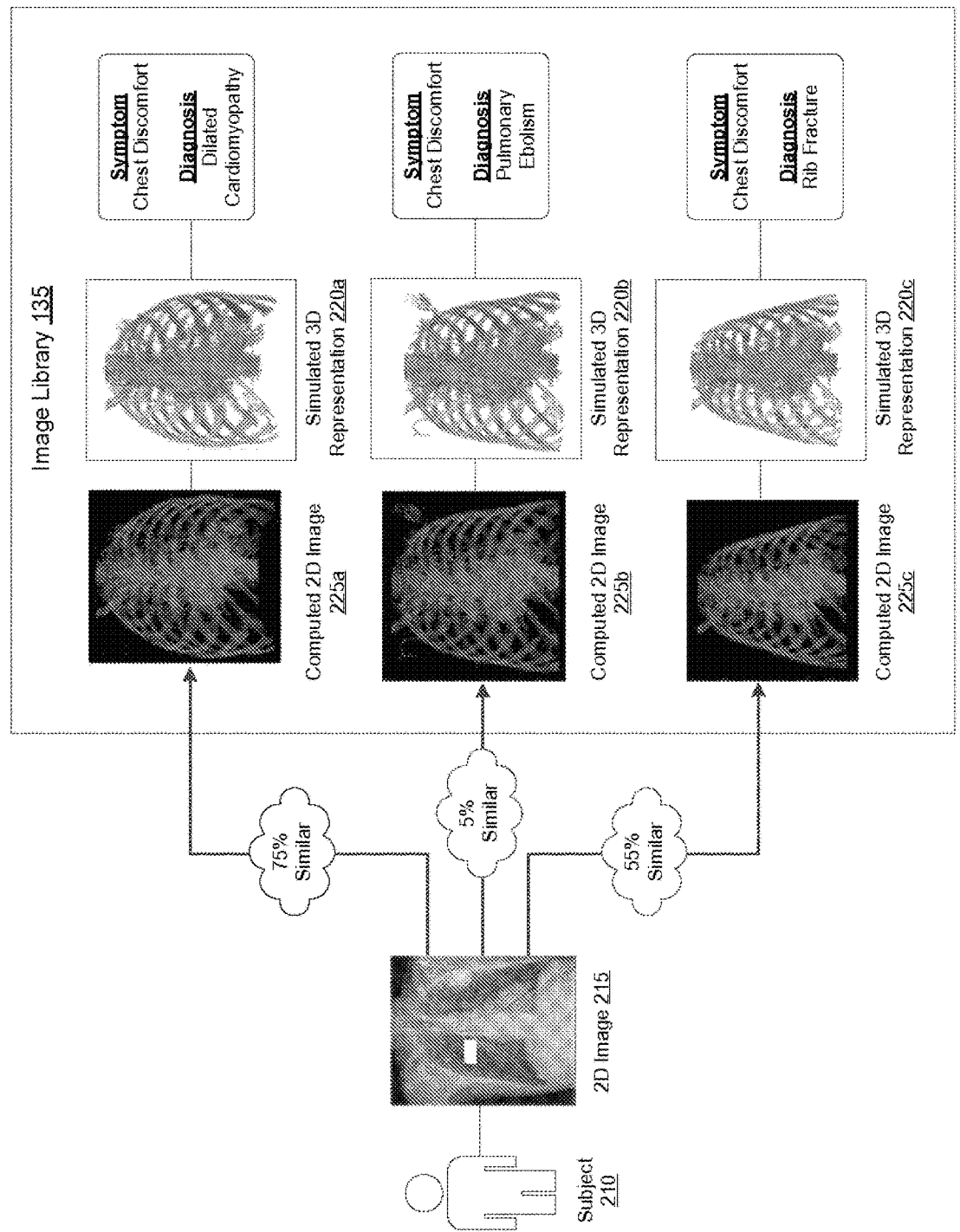
FIG. 2 depicts a block diagram illustrating a block diagram illustrating an example of identifying a simulated three-dimensional representation which most closely corresponds to a subject's internal anatomy, in accordance with some example embodiments.

To further illustrate, FIG. 2 depicts a block diagram illustrating an example of identifying a simulated three-dimensional representation corresponding to a subject's internal anatomy, in accordance with some example embodiments. Referring to FIGS. 1-2, the simulation controller 110 may receive, from the client 120, one or more two-dimensional images depicting an internal anatomy of a subject 210 including, for example, a two-dimensional image 215. The two-dimensional image 215 may be generated using a projectional radiography technique including, for example, X-rays, gamma rays, fluoroscopy, and/or the like. In some example embodiments, the simulation controller 110 may identify, based at least on the two-dimensional image 215, one or more simulated three-dimensional representations in the image library 135 that corresponds to the internal anatomy of the subject 210.

Referring again to FIG. 2, the image library 135 may include a plurality of simulated three-dimensional representations including, for example, a first simulated three-dimensional representation 220a, a second simulated three-dimensional representation 220b, a third simulated three-dimensional representation 220c, and/or the like. As shown in FIG. 2, each simulated three-dimensional representation included in the image library 135 may be associated with one or more computed two-dimensional images, each of which being generated based on a corresponding simulated three-dimensional representation. For example, FIG. 2 shows the first simulated three-dimensional representation 220a being associated with a first computed two-dimensional image 225a generated based on the first simulated three-dimensional representation 220a, the second simulated three-dimensional representation 220b being associated with a second computed two-dimensional image 225b generated based on the second simulated three-dimensional representation 220b, and the third simulated three-dimensional representation 220c being associated with a third computed two-dimensional image 225c generated based on the third simulated three-dimensional representation 220c.

The simulation controller 110 may apply one or more image comparison techniques in order to determine whether the two-dimensional image 215 matches the first computed two-dimensional image 225a associated with the first simulated three-dimensional representation 220a, the second computed two-dimensional image 225b associated with the second simulated three-dimensional representation 220b, and/or the third computed two-dimensional image 225c associated with the third simulated three-dimensional representation 220c. The one or more image comparison techniques may include scale invariant feature transform (SIFT), speed up robust feature (SURF), binary robust independent elementary features (BRIEF), oriented FAST and rotated BRIEF (ORB), and/or the like. Alternatively and/or additionally, the one or more image comparison techniques may include one or more machine learning models trained to identify similar images including, for example, autoencoders, neural networks, and/or the like.

In some example embodiments, the simulation controller 110 may apply the one or more image comparison techniques to generate a probabilistic match between the two-dimensional image 215 and one or more of the first computed two-dimensional image 225a, the second computed two-dimensional image 225b, and the third computed two-dimensional image 225c. As shown in FIG. 2, each of the first computed two-dimensional image 225a, the second computed two-dimensional image 225b, and the third computed two-dimensional image 225c may be a similarity index and/or another value indicating a closeness of the match to the two-dimensional image 215. For example, the simulation controller 110 may determine that the first computed two-dimensional image 225a is 75% similar to the two-dimensional image 215, the second computed two-dimensional image 225b is 5% similar to the two-dimensional image 215, and the third computed two-dimensional image 225c is 55% similar to the two-dimensional image 215. The simulation controller 110 may determine, based at least on the respective similarity index, that one or more of the first computed two-dimensional image 225a, the second computed two-dimensional image 225b, and the third computed two-dimensional image 225c match the two-dimensional image 215. For instance, the simulation controller 110 may determine that the first computed two-dimensional image 225a matches the two-dimensional image 215 based on the first computed two-dimensional image 225a being associated with a highest similarity index and/or the first computed two-dimensional image 225a being associated with a similarity index exceeding a threshold value.

In some example embodiments, the simulation controller 110 may identify, based at least on the computed two-dimensional images matched to the two-dimensional image 215, one or more simulated three-dimensional representations corresponding to the internal anatomy of the subject 210. For example, based on the first computed two-dimensional image 225a being determined to match the two-dimensional image 215, the simulation controller 110 may identify the first simulated three-dimensional representation 220a as corresponding to the internal anatomy of the subject 210.

Furthermore, as shown in FIG. 2, each of the first simulated three-dimensional representation 220a, the second simulated three-dimensional representation 220b, and the third simulated three-dimensional representation 220c may be associated with a diagnosis. As such, the simulation controller 110 may further determine one or more diagnosis for the subject 210 based at least on the one or more simulated three-dimensional representations determined to correspond to the internal anatomy of the subject 210. When the simulation controller 110 determines multiple diagnosis for the subject 210, each diagnosis may be associated with a probability corresponding to the similarity index between the two-dimensional image 215 and the computed two-dimensional image matched with the two-dimensional image 215. For example, based on the 75% similarity between the two-dimensional image 215 and the first computed two-dimensional image 225a, the simulation controller 110 may determine that there is a 75% chance of the subject 210 being afflicted with dilated cardiomyopathy. Alternatively and/or additionally, based on the 5% similarity between the two-dimensional image 215 and the second computed two-dimensional image 225b, the simulation controller 110 may determine that there is a 5% chance of the subject 210 being afflicted with a pulmonary embolism.

In some example embodiments, an actual diagnosis for the subject 210 may be used to at least refine one or more machine learning-based image comparison techniques for matching the two-dimensional image 215 to one or more of the first computed two-dimensional image 225a, the second computed two-dimensional image 225b, and the third computed two-dimensional image 225c. For instance, if the simulation controller 110 applying a trained machine learning model (e.g., autoencoder, neural network, and/or the like) determines that the two-dimensional image 215 is matched to the first computed two-dimensional image 225a corresponding to dilated cardiomyopathy but the actual diagnosis for the subject 210 is a rib fracture, the simulation controller 110 may at least retrain the machine learning model to correctly match the two-dimensional image 215 to the third computed two-dimensional image 225c. The machine learning model may be retrained based on additional training data that include at least some two-dimensional images that depict a rib fracture. The retraining of the machine learning model may include further updating the one or more weights and/or biases applied by the machine learning model to reduce an error in an output of the machine learning model including, for example, the mismatching of two-dimensional images depicting rib fractures.

In order to reduce the time and computation resources associated with searching the image library 135 for one or more computed two-dimensional images matching the two-dimensional image 215, the simulation controller 110 may apply one or more filters to eliminate at least some of the computed two-dimensional images from the search. For example, the computed two-dimensional images (and the corresponding simulated three-dimensional representations) included in the image library 135 may be indexed based on one or more attributes such as, for example, the demographics (e.g., age, gender, and/or the like) and/or the vital statistics (e.g., height, weight, and/or the like) of reference subjects depicted in the computed two-dimensional image. Alternatively and/or additionally, the computed two-dimensional images (and the corresponding simulated three-dimensional representations) included in the image library 135 may be indexed based on the corresponding primary symptom and/or complaint of the subject. For example, the first computed two-dimensional image 225a, the second computed two-dimensional image 225b, and the third computed two-dimensional image 225c may be indexed based on the complaint or symptom of "chest discomfort." Alternatively and/or additionally, the computed two-dimensional images (and the corresponding simulated three-dimensional representations) included in the image library 135 may be indexed based on the corresponding diagnosis and/or types of diagnosis. For instance, the first computed two-dimensional image 225a and the second computed two-dimensional image 225b may be indexed as "heart conditions" while the third computed two-dimensional image 225c may be indexed as "bone fractures."

Accordingly, instead of comparing the two-dimensional image 215 to every computed two-dimensional image included in the image library 135, the simulation controller 110 may eliminate, based on the demographics and/or the vital statistics of the subject 210, one or more computed two-dimensional images of reference subjects having different demographics and/or vital statistics than the subject 210. Alternatively and/or additionally, the simulation controller 110 may further eliminate, based on one or more symptoms of the subject 210, one or more computed two-dimensional images associated with diagnosis that are inconsistent with the symptoms of the subject 210.

Referring again to FIG. 2, the image library 135 may include a plurality of simulated three-dimensional representations including, for example, the first simulated three-dimensional representation 220a, the second simulated three-dimensional representation 220b, the third simulated three-dimensional representation 220c, and/or the like. In some example embodiments, the first simulated three-dimensional representation 220a, the second simulated three-dimensional representation 220b, and/or the third simulated three-dimensional representation 220c may be existing three-dimensional representations of the internal anatomies of one or more reference subjects including, for example, computed tomography scans, magnetic resonance imaging scans, and/or the like. The reference subjects may exhibit a variety of different anatomical attributes including, for example, variations in skeletal properties (e.g., size, abnormalities, and/or the like), organ geometry (e.g., size, relative position, and/or the like), musculature, subcutaneous fat distribution, and/or the like. As such, the first simulated three-dimensional representation 220a, the second simulated three-dimensional representation 220b, and/or the third simulated three-dimensional representation 220c may also depict a variety of different anatomical attributes.

According to some example embodiments, additional anatomical variations may be introduced computationally into the image library 135 by at least generating, based on the existing three-dimensional representations, one or more simulated three-dimensional representations that include at least variation to the internal anatomy of the corresponding reference subject. For instance, the first simulated three-dimensional representation 220a, the second simulated three-dimensional representation 220b, and/or the third simulated three-dimensional representation 220c may be generated, based on one or more existing three-dimensional representations of the internal anatomy of a reference subject, to include variations in the skeletal properties (e.g., size, abnormalities, and/or the like), organ geometries (e.g., size, relative position, and/or the like), musculature, and/or subcutaneous fat distribution of the same reference subject.

To further illustrate, FIGS. 3A-C and 4A-C depicts examples of simulated three-dimensional representations of internal anatomies, in accordance with some example embodiments. FIGS. 3A-C and 4A-C depict examples of simulated three-dimensional representations that may be generated based on existing three-dimensional representations of the internal anatomies of one or more reference subjects including, for example, computed tomography scans, magnetic resonance imaging scans, and/or the like. Furthermore, FIGS. 3A-C and 4A-C depict examples of simulated three-dimensional representations with computationally introduced anatomical variations including, for example, variations in skeletal properties (e.g., size, abnormalities, and/or the like), organ geometries (e.g., size, relative position, and/or the like), musculature, subcutaneous fat distribution, and/or the like.

For example, FIG. 3A-C depict examples of simulated three-dimensional representations of skeletal anatomy, in accordance with some example embodiments. FIG. 3A may depict a simulated three-dimensional representation 310 of the skeletal anatomy of a first reference subject who is a 65 years old, male, 6 feet 5 inches tall, weighing 220 pounds, and having severe congestive heart failure with a left ventricular ejection fraction of 25%. FIG. 3B may depict a simulated three-dimensional representation 320 of the skeletal anatomy of a second reference subject who is 70 years old, female, 5 feet 7 inches tall, weighing 140 pounds, and having moderate chronic systolic congestive heart failure with a left ventricular ejection fraction of 35%. Furthermore, FIG. 3C may depict a simulated three-dimensional representation 330 of the skeletal anatomy of a third reference subject who is 18 years old, weighing 120 pounds, and having a congenital heart disease with an ejection fraction of 45%. As noted, FIGS. 3A-C may be indexed based on one or more attributes including, for example, the demographics (e.g., age, gender, and/or the like), the vital statistics (e.g., weight, height, and/or the like), and/or the condition of the corresponding reference subject.

Figure 4A:
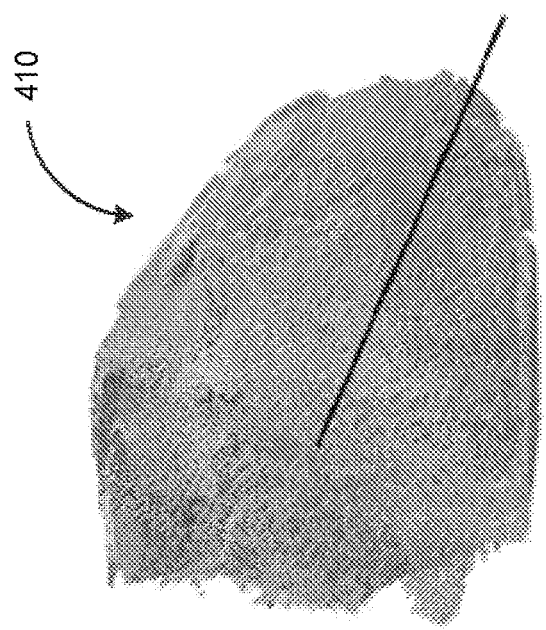
FIG. 4A depicts an example of a simulated three-dimensional representation of a cardiac anatomy of a reference subject, in accordance with some example embodiments.
Figure 4B:
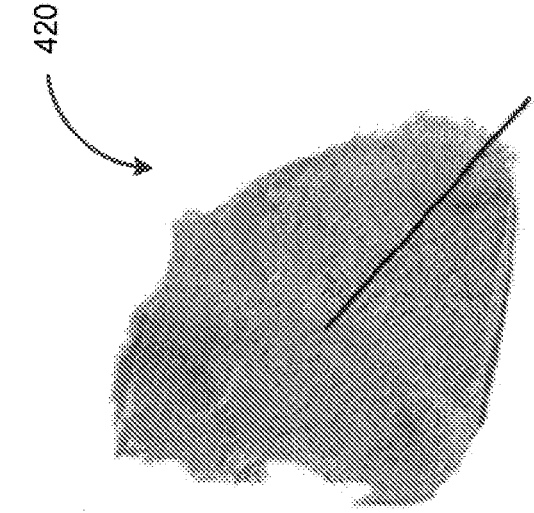
FIG. 4B depicts another example of a simulated three-dimensional representation of a cardiac anatomy of a reference subject, in accordance with some example embodiments.
Figure 4C:
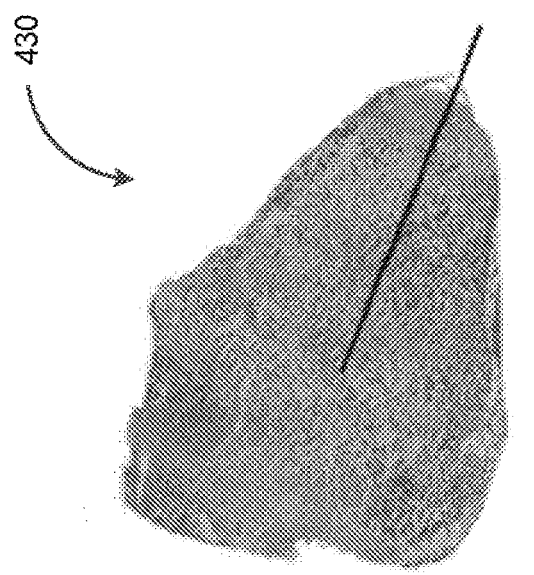
FIG. 4C depicts another example of a simulated three-dimensional representation of a cardiac anatomy of a reference subject, in accordance with some example embodiments.

FIGS. 4A-C depicts examples of simulated three-dimensional representations of cardiac anatomies, in accordance with some example embodiments. FIG. 4A depicts a simulated three-dimensional representation 410 of a heart with moderate congestive heart failure, an ejection fraction of 40%, and a ventricular axis of 30 degrees (shown as a black line) in the frontal plane. FIG. 4B depicts a simulated three-dimensional representation 420 of a heart with a normal ejection fraction of 57% and a ventricular axis of 45 degrees (shown as a black line) in the frontal plane. Furthermore, FIG. 4C depicts a simulated three-dimensional representation 420 of a heart with severe left ventricular dysfunction, an ejection fraction of 20%, and a ventricular axis of 20 degrees (shown as a black line) in the frontal plane. FIGS. 4A-C may also be indexed based on one or more attributes including, for example, the demographics (e.g., age, gender, and/or the like), the vital statistics (e.g., weight, height, and/or the like), and/or the condition of the corresponding reference subject.

As noted, the simulated three-dimensional representations included in the image library 135 may be used to generate the computed two-dimensional images included in the image library 135. For example, referring again to FIG. 2, the first computed two-dimensional image 225a may be generated based on the first simulated three-dimensional representation 220a, the second computed two-dimensional image 225b may be generated based on the second simulated three-dimensional representation 220b, and the third computed two-dimensional image 225c may be generated based on the third simulated three-dimensional representation 220c.

The computed two-dimensional images included in the image library 135 may correspond to radiograph images (e.g., X-ray images, gamma ray images, fluoroscopy images, and/or the like), which are typically captured using a projectional, or 2-dimensional radiography techniques, in which at least a portion of a subject is exposed to electromagnetic radiation (e.g., X-rays, gamma rays, and/or the like). As such, in some example embodiments, a computed two-dimensional image may be generated by at least simulating the effects of being exposed to a radiation source. For example, the computed two-dimensional image based at least on a density and/or radiation transmissivity of the different tissues included in the simulated three-dimensional representation.

Figure 5:
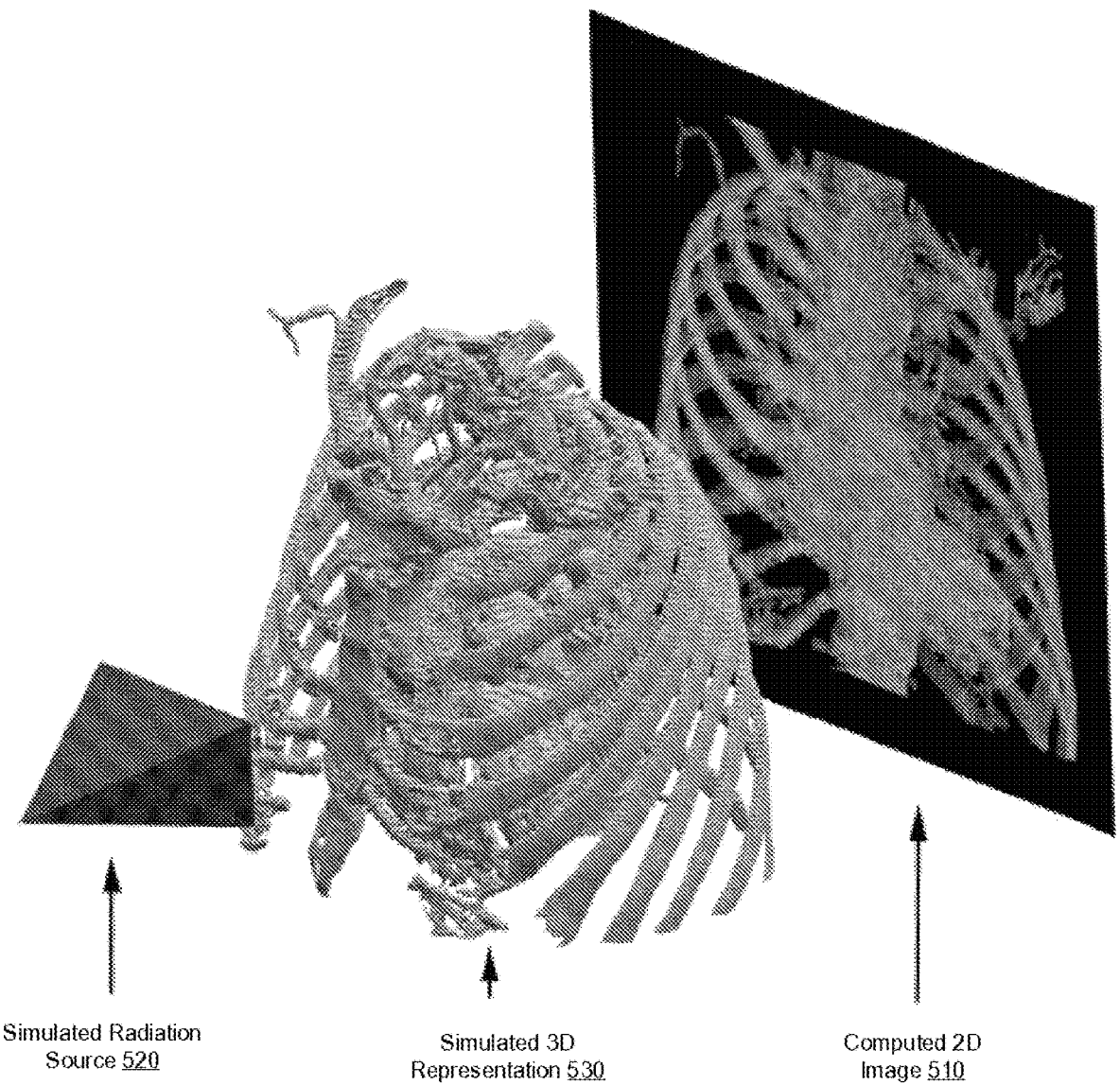
FIG. 5 depicts an example of a technique for generating a computed two-dimensional image, in accordance with some example embodiments.

To further illustrate, FIG. 5 depicts an example of a technique for generating a computed two-dimensional image, in accordance with some example embodiments. Referring to FIG. 5, a computed two-dimensional image 510 may be generated (e.g. using the software Blender (Blender Foundation, Amsterdam, Netherlands)) by at least simulating the effects of exposing, to a simulated radiation source 520 (e.g. light), a simulated three-dimensional representation 530 of an internal anatomy (e.g., a thoracic cavity and/or the like). The computed two-dimensional image 510 may be generated by at least determining, based at least on a density and/or transmissivity of the different tissues included in the simulated three-dimensional representation 530, a quantity of simulated radiation (e.g., from the simulated radiation source 520) that is able to pass through the different tissues included in the simulated three-dimensional representation 530 onto a simulated surface. An image of this project is then recorded and further processed (e.g. white-black inversion) to form the computed two-dimensional image 510.

In some example embodiments, a view of the simulated three-dimensional representation 530 (e.g., straight anterior-posterior, anterior oblique, and/or the like) that is captured in the computed two-dimensional image 510 may be varied by at least varying a position and/or an orientation of the simulated radiation source 520 relative of the simulated three-dimensional representation 530. Accordingly, multiple computed two-dimensional image may be generated for each simulated three-dimensional representation in order to capture different views of the simulated three-dimensional representation including, for example, a left anterior oblique view, a right anterior oblique view, a straight anterior-posterior view, and/or the like.

Figure 6B:
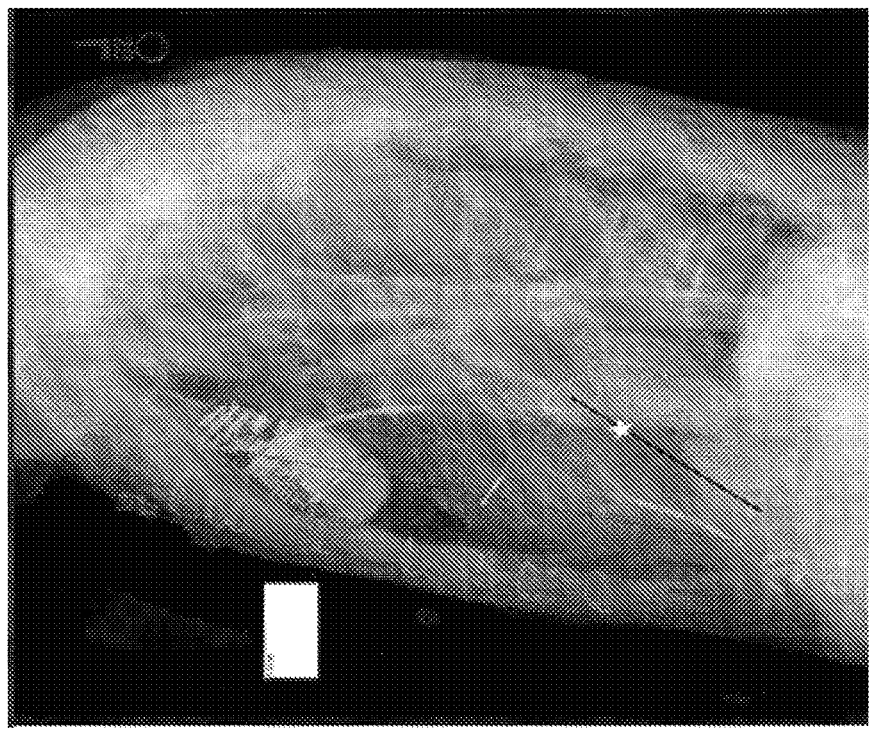
FIG. 6B depicts an example of a clinical, two-dimensional lateral chest x-ray image showing subject anatomy, the presence of an implantable cardioverter-defibrillator, and the positions of body surface electrodes, in accordance with some example embodiments.
Figure 6A:
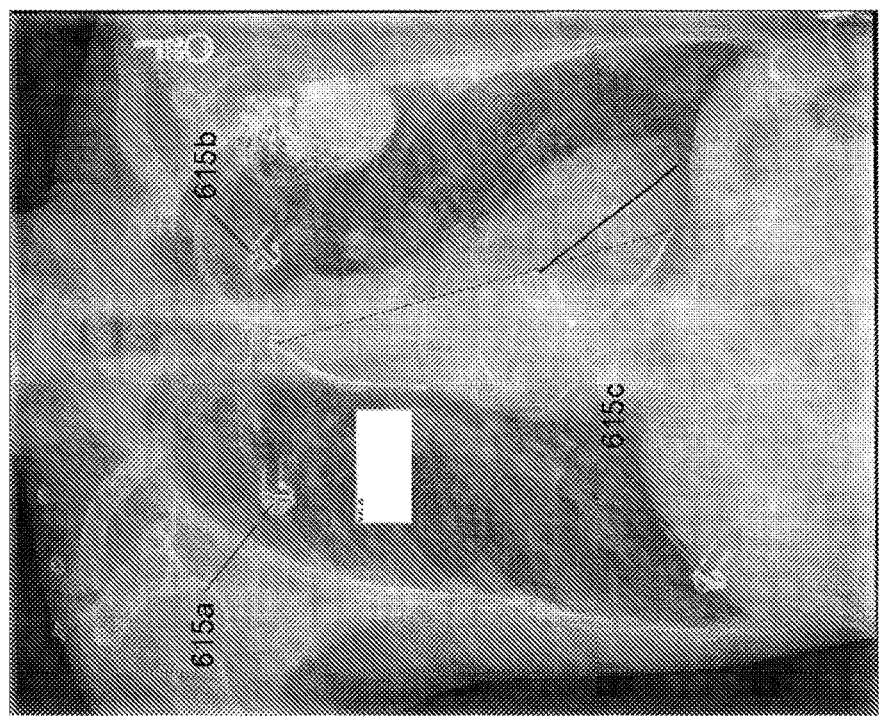
FIG. 6A depicts an example of a clinical, two-dimensional anteroposterior (AP) chest x-ray image showing subject anatomy, the presence of an implantable cardioverter-defibrillator, and the positions of body surface electrodes, in accordance with some example embodiments.

As noted, the electrical activities of an organ (e.g., heart, brain, and/or the like) is typically measured by a recording device one or more body surface leads, which may be surface electrodes configured to measure voltage changes on the surface of the subject's skin corresponding to the electrical activities of the organ. For example, FIG. 6A depicts an example of a clinical two-dimensional image 610 showing a posterior-anterior (PA) view. Notably, FIG. 6A depicts the positions of a number of surface electrodes including, for example, a first surface electrode 615a, a second surface electrode 615b, and a third surface electrode 615c. It should be appreciated that one or more of the first surface electrode 615a, the second surface electrode 615b, and the third surface electrode 615c may be in a non-standard positions. FIG. 6B depicts another example of a clinical two-dimensional image 620 showing a left lateral view of the same subject. Again, the positions of several surface electrodes may also be observed in the clinical two-dimensional image 620.

Figure 7:
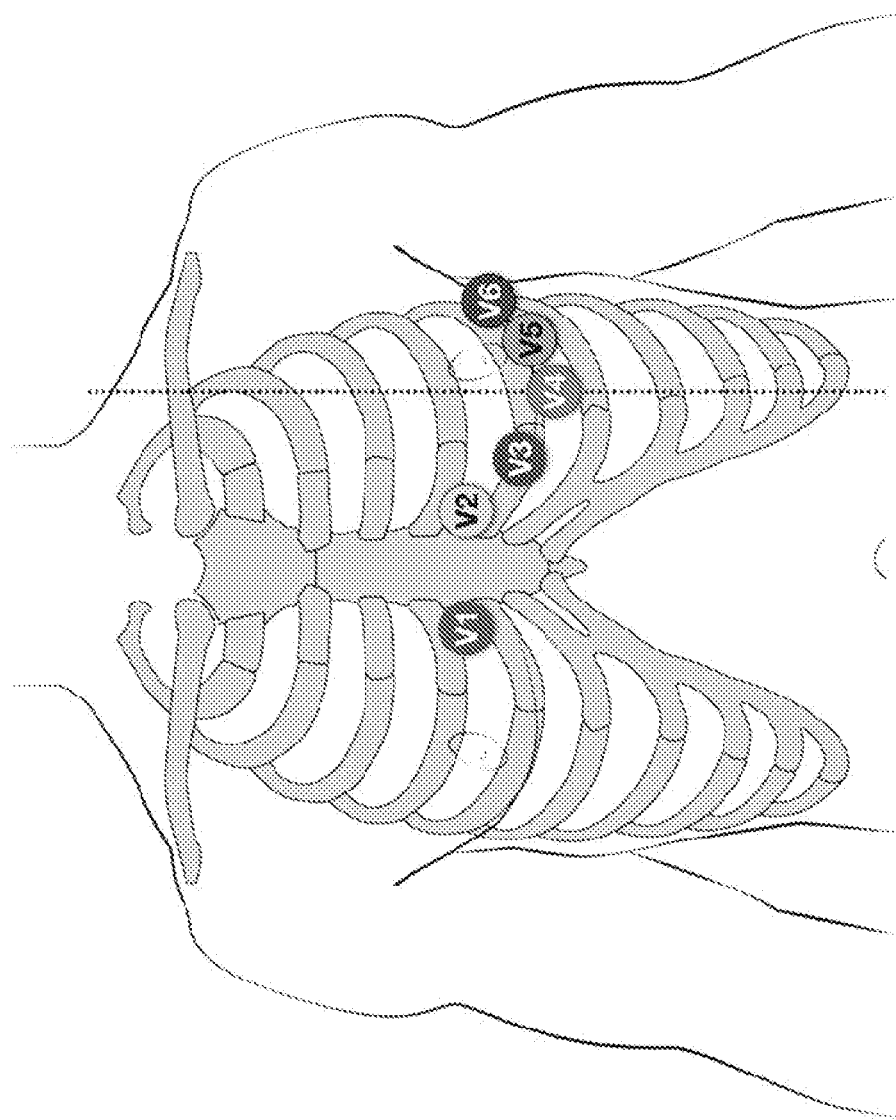
FIG. 7 depicts an example of the standard positioning of body surface electrodes (e.g the precordial leads for a 12-lead electrocardiogram) for measuring the electrical activities of an organ (e.g. the heart), in accordance with some example embodiments.
Figure 8:
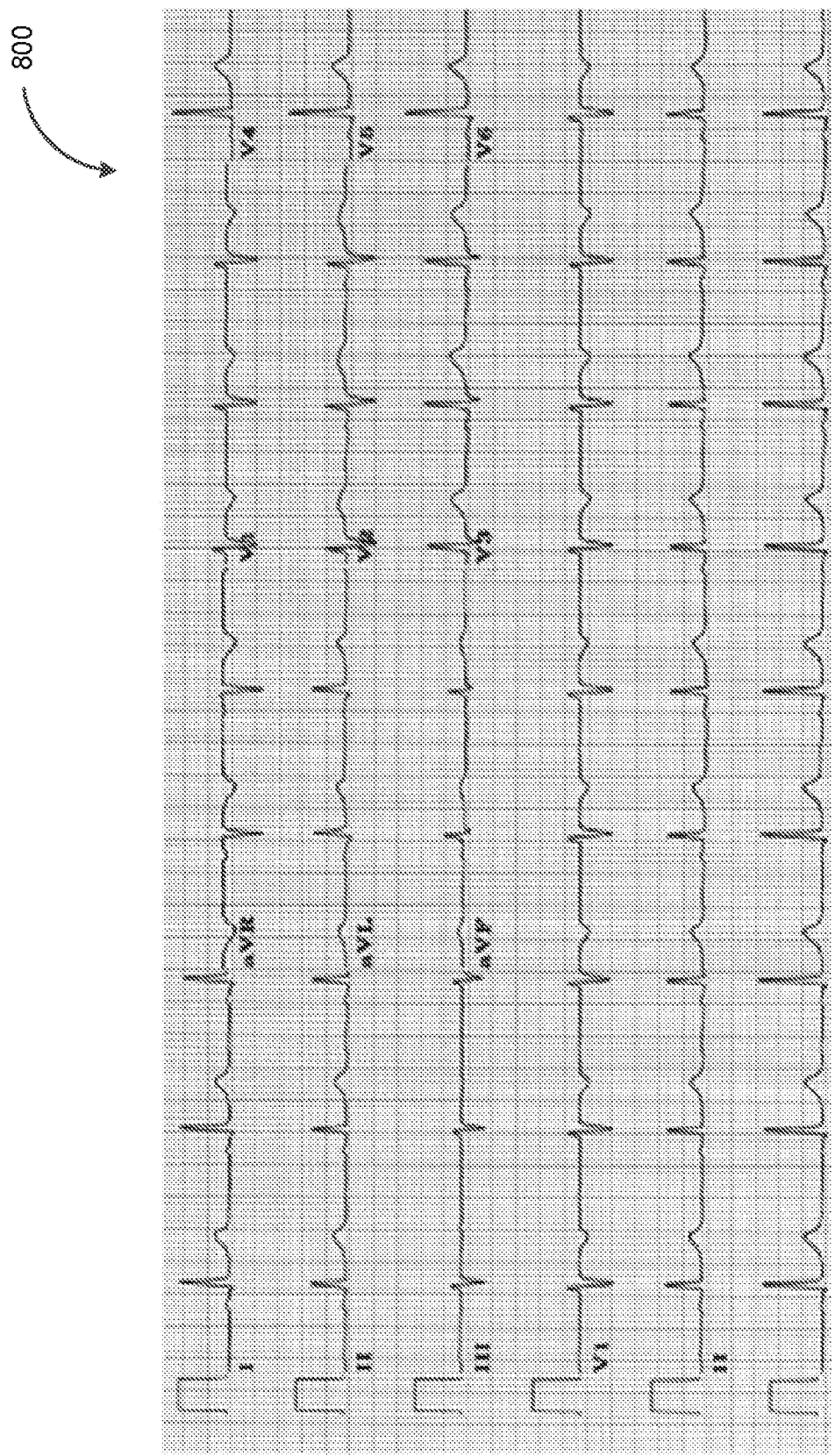
FIG. 8 depicts an example of an output from a recording device measuring the electrical activities of an organ (e.g. a standard 12-lead electrocardiogram), in accordance with some example embodiments.

Additionally, FIG. 7 depicts an example of leads for measuring the electrical activities of the heart. As shown in FIG. 7, a plurality of leads (e.g., V1, V2, V3, V4, V5, and V6) may be placed on the surface of the subject's skin. Each of the plurality of leads may be configured to measure a voltage change on the surface of the subject's skin that corresponds to the electrical activities of the subject's heart including, for example, the dipole that is created due to the successive depolarization and repolarization of the heart. The signal from each lead may be recorded, in combination with one or more other leads, to generate, for example, the electrocardiogram 800 shown in FIG. 8, demonstrating normal sinus rhythm.

In some example embodiments, the simulation controller 110 may be further configured to simulate, based on a computed two-dimensional image and/or a simulated three-dimensional representation corresponding to a subject's internal anatomy, the electrical activities of an organ (e.g., heart, brain, gastrointestinal system, and/or the like). After determining the placement of each lead in a simulated recording device based on a computed two-dimensional image of the subject's internal anatomy as described previously, the output for the simulated recording device (e.g., the electrical signals that are detected at each lead) may be determined based on the corresponding simulated three-dimensional representation of the subject's internal anatomy to generate, for example, a simulated electrocardiogram, a simulated electroencephalogram, and/or the like. For instance, the spread of an electric potential across the subject's heart as well as the corresponding signals that may be detected on the surface of the subject's skin may be simulated based at least on the subject's anatomical attributes (e.g., skeletal properties, organ geometry, musculature, subcutaneous fat distribution, and/or the like) indicated by the simulated three-dimensional representation corresponding to the subject's internal anatomy.

Determining the relationship between the target organ's simulated electrical activity and the simulated body surface electrode readings, a subject-specific transformation matrix that accounts for variations in lead placement and subject anatomy may be computed. This subject-specific transformation matrix, or correction matrix, may be used to more accurately determine the precise electrical activation pattern and orientation of the organ. For example, the subject-specific transformation matrix may be applied to generate a corrected electrogram and/or a corrected vectorgram (e.g. a corrected electrocardiogram, a corrected electroencephalogram, a corrected vectorcardiogram, and/or the like). The corrected electrogram may lead to improved diagnostic output and improved mapping of the source of the cardiac arrhythmia.

Figure 9A:
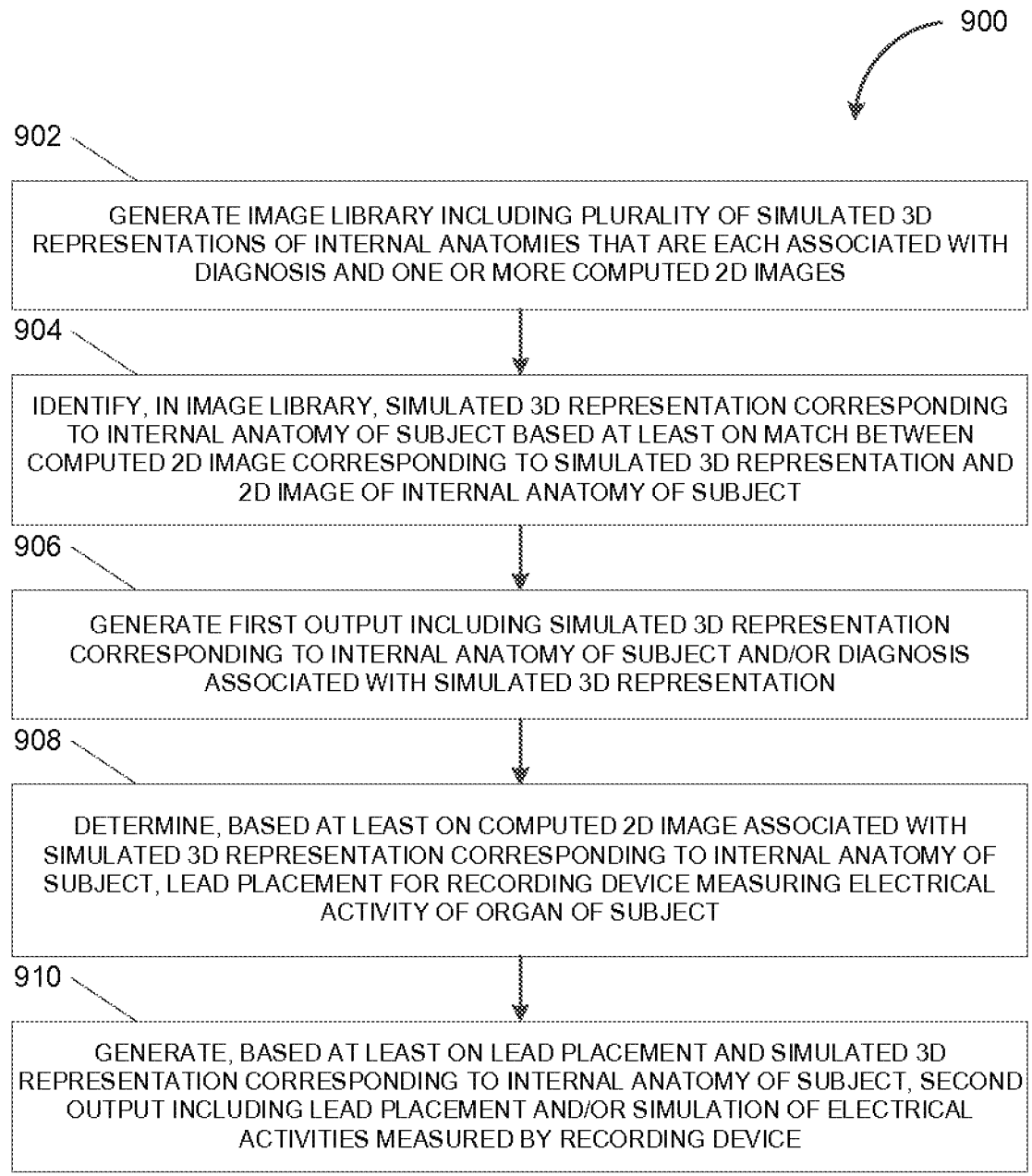
FIG. 9A depicts a flowchart illustrating an example of an imaging process, in accordance with some example embodiments.

FIG. 9A depicts a flowchart illustrating an example of an imaging process 900, in accordance with some example embodiments. Referring to FIGS. 1 and 9A, the process 900 may be performed by the simulation controller 110. For example, the simulation controller 110 may perform the imaging process 900 in order to generate a three-dimensional representation of an internal anatomy of the subject 210 by at least identifying a simulated three-dimensional representation in the image library 135 that corresponds to the internal anatomy of the subject 210. Alternatively and/or additionally, the imaging process 900 may be performed to determine, based on the simulated three-dimensional representation corresponding to the internal anatomy of the subject 210, a diagnosis for the subject 210. Furthermore, in some example embodiments, the simulation controller 100 may perform the imaging process 900 in order to simulate the electrical activities of one or more organs of the subject 210.

At 902, the simulation controller 110 may generate an image library including a plurality of simulated three-dimensional representations of internal anatomies that are each associated with a diagnosis and one or more computed two-dimensional images. For example, as shown in FIG. 2, the image library 135 may include a plurality of simulated three-dimensional representations including, for example, the first simulated three-dimensional representation 220a, the second simulated three-dimensional representation 220b, the third simulated three-dimensional representation 220c, and/or the like. The first simulated three-dimensional representation 220a, the second simulated three-dimensional representation 220b, and/or the third simulated three-dimensional representation 220c may also depict a variety of different anatomical attributes. For instance, the first simulated three-dimensional representation 220a, the second simulated three-dimensional representation 220b, and/or the third simulated three-dimensional representation 220c may be existing three-dimensional representations of the internal anatomies of one or more reference subjects exhibiting a variety of different anatomical attributes including, for example, variations in skeletal properties (e.g., size, abnormalities, and/or the like), organ geometry (e.g., size, relative position, and/or the like), musculature, subcutaneous fat distribution, and/or the like. Alternatively and/or additionally, one or more anatomical variations may be introduced computationally into the first simulated three-dimensional representation 220a, the second simulated three-dimensional representation 220b, and/or the third simulated three-dimensional representation 220c.

In some example embodiments, the simulated three-dimensional representations included in the image library 135 may be used to generate the computed two-dimensional images included in the image library 135. For example, referring again to FIG. 2, the first computed two-dimensional image 225a may be generated based on the first simulated three-dimensional representation 220a, the second computed two-dimensional image 225b may be generated based on the second simulated three-dimensional representation 220b, and the third computed two-dimensional image 225c may be generated based on the third simulated three-dimensional representation 220c.

The first computed two-dimensional image 225a, the second computed two-dimensional image 225b, and the third computed two-dimensional image 225c may each be generated by exposing, to a simulated radiation source, the corresponding first simulated three-dimensional representation 220a, the second simulated three-dimensional representation 220b, and the third simulated three-dimensional representation 220c. For instance, the first computed two-dimensional image 225a may be generated by at least determining, based at least on a density and/or transmissivity of the different tissues included in the first simulated three-dimensional representation 220a, a quantity of radiation (e.g., from a simulated radiation source) that is able to pass through the different tissues included in the first simulated three-dimensional representation 220a to form the first computed two-dimensional image 225a. Alternatively and/or additionally, the second computed two-dimensional image 225b may be generated by at least determining, based at least on a density and/or transmissivity of the different tissues forming each of the anatomical structures (e.g., organs) included in the second simulated three-dimensional representation 220b, a quantity of radiation (e.g., from a simulated radiation source) that is able to pass through the different tissues included in the second simulated three-dimensional representation 220b to form the second computed two-dimensional image 225b.

Furthermore, in some example embodiments, each of the simulated three-dimensional representations and the corresponding computed two-dimensional images included in the image library 135 may be associated with a primary symptom or complaint as well as a diagnosis. For example, the first computed two-dimensional image 225a, the second computed two-dimensional image 225b, and the third computed two-dimensional image 225c may be associated with the complaint or symptom of "chest discomfort." Moreover, the first simulated three-dimensional representation 220a (and the first computed two-dimensional image 225a) may be associated with a diagnosis of dilated cardiomyopathy, the second simulated three-dimensional representation 220b (and the second computed two-dimensional image 225b) may be associated with a diagnosis of a pulmonary embolism, and the third simulated three-dimensional representation 220c (and the third computed two-dimensional image 225c) may be associated with a diagnosis of a rib fracture.

At 904, the simulation controller 110 may identify, in the image library, a simulated three-dimensional representation corresponding to an internal anatomy of a subject based at least on a match between a computed two-dimensional image corresponding to the simulated three-dimensional representation and a two-dimensional image of the internal anatomy of the subject. For example, the simulation controller 110 may apply one or more image comparison techniques in order to determine whether the two-dimensional image 215 matches the first computed two-dimensional image 225a associated with the first simulated three-dimensional representation 220a, the second computed two-dimensional image 225b associated with the second simulated three-dimensional representation 220b, and/or the third computed two-dimensional image 225c associated with the third simulated three-dimensional representation 220c. The one or more image comparison techniques may include scale invariant feature transform (SIFT), speed up robust feature (SURF), binary robust independent elementary features (BRIEF), oriented FAST and rotated BRIEF (ORB), and/or the like. Alternatively and/or additionally, the one or more image comparison techniques may include one or more machine learning models trained to identify similar images including, for example, autoencoders, neural networks, and/or the like.

In some example embodiments, the match between the two-dimensional image 215 and one or more of the first computed two-dimensional image 225a, the second computed two-dimensional image 225b, and the third computed two-dimensional image 225c may be probabilistic. For example, as shown in FIG. 2, the simulation controller 110 may determine that the first computed two-dimensional image 225a is 75% similar to the two-dimensional image 215, the second computed two-dimensional image 225b is 5% similar to the two-dimensional image 215, and the third computed two-dimensional image 225c is 55% similar to the two-dimensional image 215. The simulation controller 110 may determine, based at least on a computed two-dimensional image having a highest similarity index and/or a similarity index exceeding a threshold value, that one or more of the first computed two-dimensional image 225a, the second computed two-dimensional image 225b, and the third computed two-dimensional image 225c match the two-dimensional image 215.

In some example embodiments, the time and computation resources associated with searching the image library 135 for one or more computed two-dimensional images matching the two-dimensional image 215 may be reduced by applying one or more filters to eliminate at least some of the computed two-dimensional images from the search. For example, the computed two-dimensional images (and the corresponding simulated three-dimensional representations) included in the image library 135 may be indexed based on one or more attributes such as, for example, the demographics (e.g., age, gender, and/or the like) and/or the vital statistics (e.g., height, weight, and/or the like) of reference subjects depicted in the computed two-dimensional image. Alternatively and/or additionally, the computed two-dimensional images (and the corresponding simulated three-dimensional representations) included in the image library 135 may be indexed based on the corresponding diagnosis and/or types of diagnosis.

Accordingly, instead of comparing the two-dimensional image 215 to every computed two-dimensional image included in the image library 135, the simulation controller 110 may eliminate, based on the demographics, the vital statistics, and/or the symptoms of the subject 210, one or more computed two-dimensional images of reference subjects having different demographics, different vital statistics, and/or diagnosis that are inconsistent with the symptoms of the subject 210. For example, if the subject 210 exhibits symptoms consistent with a heart condition, the image library 315 may exclude, from the search of the image library 135, the third computed two-dimensional image 225c based at least on the third computed two-dimensional image 225c being associated with a diagnosis (e.g., rib fracture) that is inconsistent with the symptoms of the subject 210.

At 906, the simulation controller 110 may generate a first output including the simulated three-dimensional representation corresponding to the internal anatomy of the subject and/or a diagnosis associated with the simulated three-dimensional representation. For example, in response to the two-dimensional image 215 of the subject 210 being matched to the first computed two-dimensional image 225a, the simulation controller 110 may generate an output including the first simulated three-dimensional representation 220a and/or the diagnosis (e.g., dilated cardiomyopathy) associated with the first simulated three-dimensional representation 220a. The simulation controller 110 may generate the output to also include a value indicative of the closeness of the match (e.g., 75% similar) between the two-dimensional image 215 and the first computed two-dimensional image 225a. Alternatively and/or additionally, the simulation controller 110 may generate the output to include a value indicative of a probability of the diagnosis associated with the first simulated three-dimensional representation 220a (e.g., 75% chance of dilated cardiomyopathy).

It should be appreciated that the simulation controller 110 may send, to the client 120, the first output including the simulated three-dimensional representation corresponding to the internal anatomy of the subject and/or a diagnosis associated with the simulated three-dimensional representation. Alternatively and/or additionally, the simulation controller 110 may generate a user interface configured to display, at the client 120, the first output including the simulated three-dimensional representation corresponding to the internal anatomy of the subject and/or a diagnosis associated with the simulated three-dimensional representation.

At 908, the simulation controller 110 may determine, based at least on one or more clinical two-dimensional images of the subject and the simulated three-dimensional representation corresponding to the internal anatomy of the subject, a lead placement for a recording device measuring an electrical activity of an organ of the subject. For example, the lead placement for electrocardiography (ECG) to measure the electrical activities of the heart and/or electroencephalography (EEG) to measure the electrical activities of the brain may be determined based on the images 610 and 620 corresponding to FIGS. 9C and 9D.

At 910, the simulation controller 110 may generate, based at least on the lead placement and the simulated three-dimensional representation corresponding to the internal anatomy of the subject, a second output including the lead placement and a simulation of the electrical activities measured by the recording device. For example, in some example embodiments, the simulation controller 110 may further determine, based at least on the lead placement (e.g., determined at operation 908) and the first simulated three-dimensional representation 220a corresponding to the internal anatomy of the subject 210, a simulated electrocardiogram (ECG) depicting the electrical activities of the heart and/or a simulated electroencephalography (EEG) depicting the electrical activities of the brain. The simulated electrocardiogram (ECG) and/or the simulated electroencephalography (EEG) may depict the signals that may be measured by each lead placed in accordance with the placement determined in operation 908. For instance, a simulated electrocardiogram may depict the voltage changes that may be measured by each lead on the surface of the subject's skin. These voltage changes may correspond to the electrical activities of the subject's heart including, for example, the dipole that is created due to the successive depolarization and repolarization of the heart.

In some example embodiments, the simulation controller 110 may send, to the client 120, the second output including the lead placement and/or the simulation of the electrical activities measured by the recording device. Alternatively and/or additionally, the simulation controller 110 may generate a user interface configured to display, at the client 120, the second output including the lead placement and/or the simulation of the electrical activities measured by the recording device.

Figure 9B:
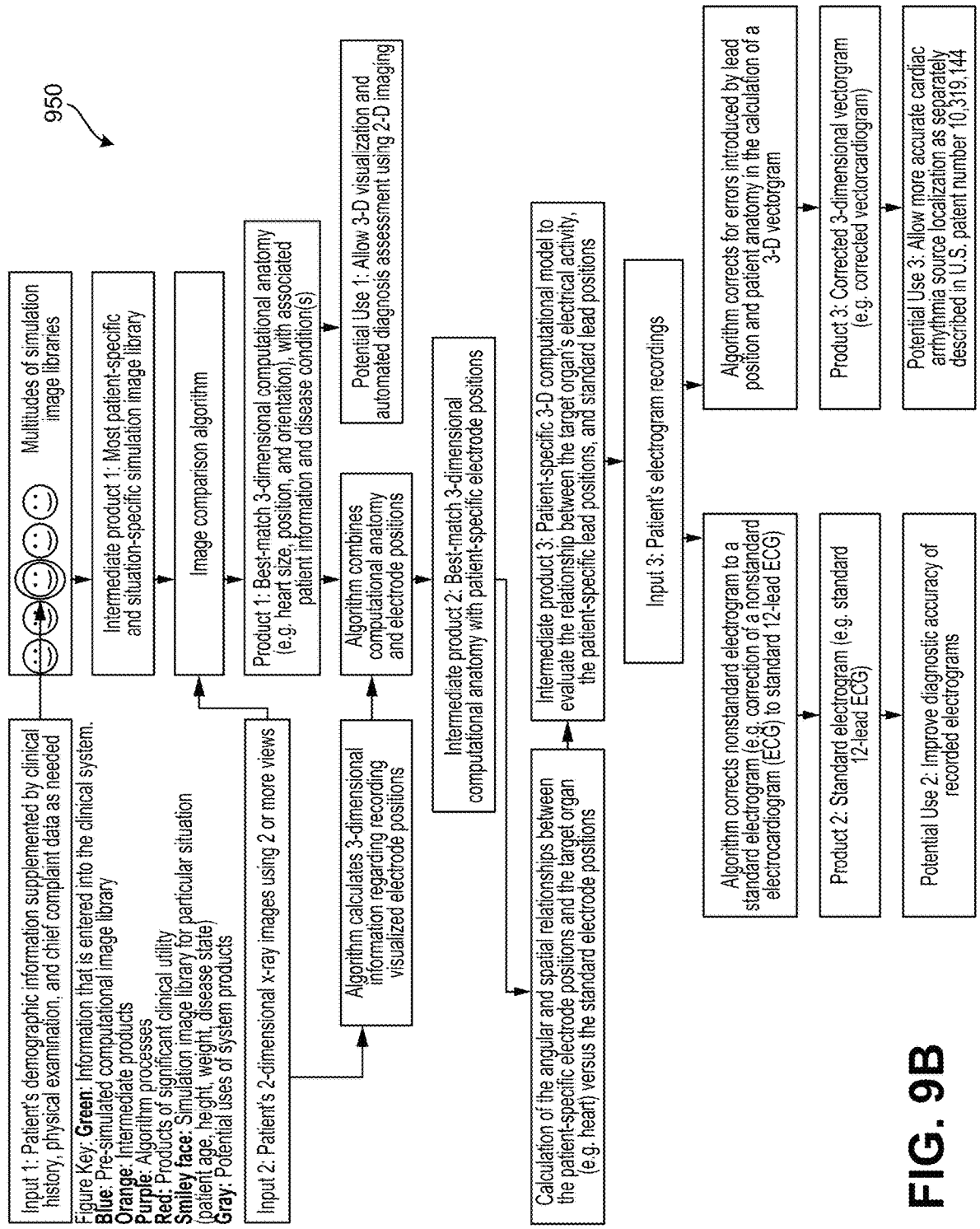
FIG. 9B depicts a flowchart illustrating an example of an imaging process and generation of a computational model of a subject, in accordance with some example embodiments.

FIG. 9B depicts a flowchart illustrating another example of an imaging process 950, in accordance with some example embodiments. Referring to FIGS. 1 and 9B, the process 950 may be performed by the simulation controller 110. For example, the simulation controller 110 may perform the imaging process 950 in order to generate a three-dimensional representation of an internal anatomy of the subject 210 by at least identifying a simulated three-dimensional representation in the image library 135 that corresponds to the internal anatomy of the subject 210. Alternatively and/or additionally, the imaging process 950 may be performed to determine, based on the simulated three-dimensional representation corresponding to the internal anatomy of the subject 210, a diagnosis for the subject 210. Furthermore, in some example embodiments, the simulation controller 100 may perform the imaging process 950 in order to simulate the electrical activities of one or more organs of the subject 210 to produce a customized simulation environment of the subject including the electrical activity of an organ and the simulated body surface electrical activity including the simulated body surface recordings detected by the recording electrodes (bottom right box labelled Product 2).

As shown in FIG. 9B, the simulation controller 110 may receive inputs including (1) demographic and clinical information such as age, weight, sex, clinical situation, and symptoms; (2) two-dimensional clinical images from one or more views (examples include FIGS. 6A and 6B); and (3) subject electrical recordings (e.g. a clinical electrogram or vectorgram such as, for example, a clinical electrocardiogram, electroencephalogram, vectorcardiogram, and/or the like).

In some example embodiments, the image library 135 may be created from subject-derived, three-dimensional representations of subject anatomy. The simulated two-dimensional images may be created to include simulated two-dimensional images from different angles. Moreover, the simulated two-dimensional images and the corresponding three-dimensional models may be indexed with one or more subject attributes including, for example, weight, height, sex, clinical situation, symptoms, and/or the like.

For a specific subject, the simulation controller may receive inputs including, for example, the subject's age, weight, height, sex, clinical situation, and symptoms (FIG. 9B, Input 1). The simulation controller 110 may select an appropriate simulation library (FIG. 9B, face symbol) for the intended instance (FIG. 9B, Intermediate Product 1). Furthermore, the simulation controller 110 may receive one or more two-dimensional images of the subject's anatomy (FIG. 9B, Input 2) and compares these two-dimensional images to the computed two-dimensional images included in the image library 135. Computed two-dimensional images with the highest correlation with the subject's two-dimensional images may be identified. A combination of the highest matching computed two-dimensional images, the corresponding three-dimensional representations, and the associated case information (e.g., demographics, clinical situation, diagnosis, and/or the like) may be output by the simulation controller 110 (FIG. 9B, Product 1).

In some example embodiments, the simulation controller 110 may further identify the locations of one or more leads (e.g., pairs of surface electrodes) in the subject's two-dimensional images and calculates positions of the leads relative to the subject's skin (FIG. 9B, Intermediate Product 2). The simulation controller 110 may compute the angular and spatial relationship between the actual lead placement, the target organ (e.g., heart, brain, and/or the like), and the position of standard lead placements, thereby creating a subject-specific three-dimensional simulation environment suitable for simulating the electrical activities of the target organ (FIG. 9B, Intermediate Product 3).

A simulation of the electrical activation of the organ may be performed within the subject-specific three-dimensional simulation environment including the three-dimensional representation corresponding to the subject's internal anatomy. For example, the simulated electrical field from the organ may be calculated as the electrical field diffuses through body tissues to the skin surface. Simulated recordings at both the subject-specific electrode positions and standard electrode positions may be computed. The relationship between the organ's electrical activation and the body surface recordings may be used to compute correction function for each electrode site (e.g. a "nonstandard-to-standard correction matrix") and for correcting between the organ's electrical activation pattern and that observed at the body surface (e.g. a "vectorgram correction matrix").

The subject's recorded electrogram is then analyzed. Using the correction matrices, a standardized electrogram (e.g. FIG. 9B, Product 2) and/or a spatially and rotationally-corrected vectorgram (e.g. FIG. 9B, Product 3) may be generated. The standardized electrogram may be used to increase the diagnostic accuracy of the recorded electrogram while the corrected vectorgram may be used to increase the accuracy of an arrhythmia source localization system.

It should be appreciated that the simulation controller 110 may operate (1) to create a simulated three-dimensional representation of a subject's internal anatomy as well as a computational assessment of diagnosis probability (FIG. 9B: Potential Use 1); (2) to convert a nonstandard electrogram (e.g. nonstandard 12-lead electrocardiogram) to a standard electrogram (e.g. standard 12-lead electrocardiogram) (FIG. 9B: Potential Use 2) to improve the diagnostic accuracy of the electrogram; and (3) to correct for subject-specific variations in electrode position and subject anatomy in the calculation of a three-dimensional vectorgram (e.g., vectorcardiogram and/or the like) to permit an accurate electrical source mapping (e.g. for use in arrhythmia source localization) (FIG. 9B, Potential Use 3).

Figure 9C:
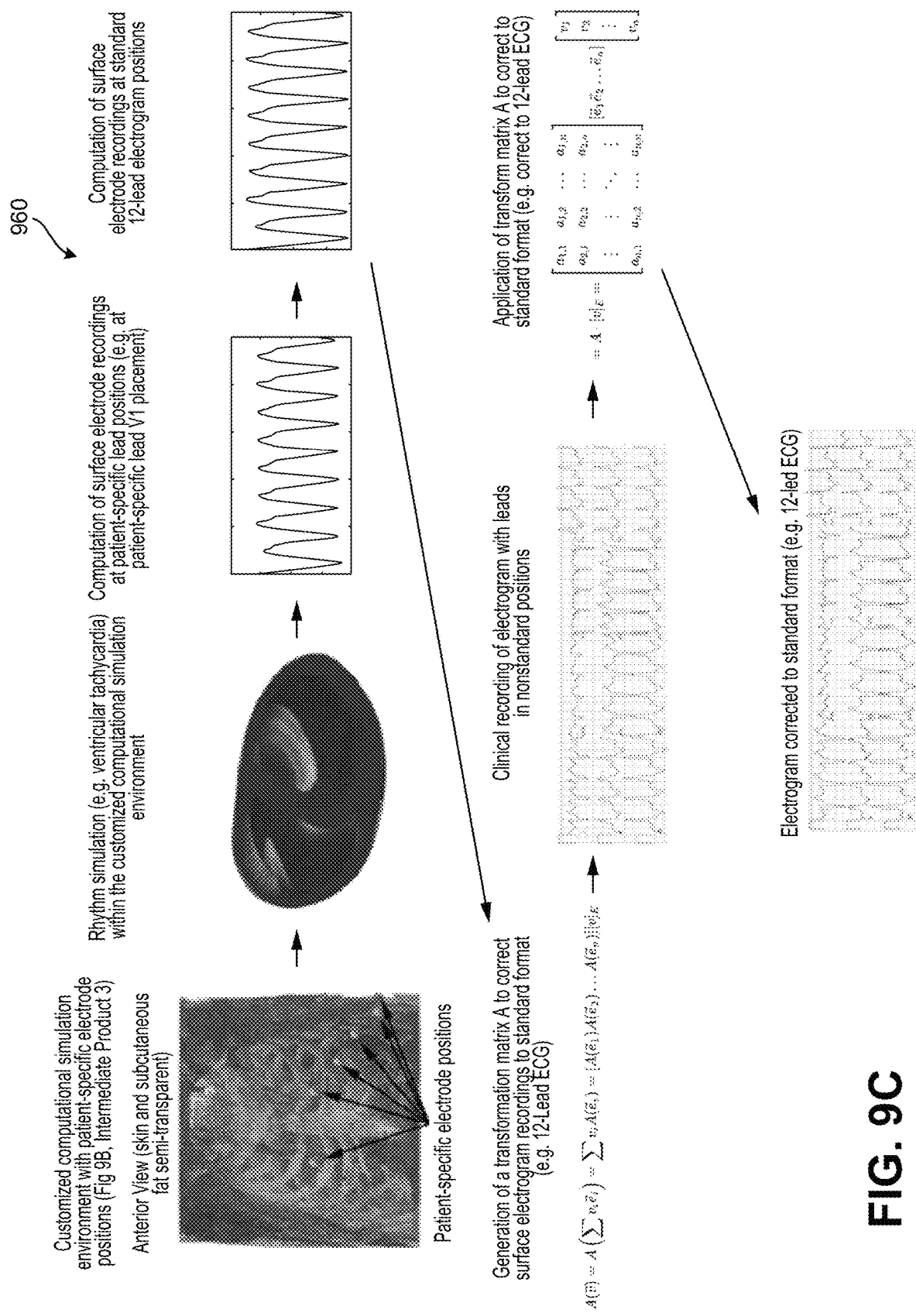
FIG. 9C depicts a diagram illustrating an example of process for generating a corrected electrogram, in accordance with some example embodiments.

FIG. 9C depicts a block diagram illustrating an example of process 960 for generating a corrected electrogram, in accordance with some example embodiments. Referring to FIGS. 1 and 9C, the process 960 may be performed by the simulation controller 110 in order to generate a corrected electrogram that accounts for variations in lead placement and subject anatomy.

As shown in FIG. 9C, the simulation controller 110 may generate, based at least on a simulated three-dimensional representation of the subject's internal anatomy (e.g., thorax cavity and/or the like), a rhythm simulation (e.g., ventricular tachycardia and/or the like). The simulated three-dimensional representation of the subject's internal anatomy may be identified based on one or more clinical two-dimensional images of the subject's internal anatomy. Moreover, a first plurality of surface electrode recordings may be computed based on the rhythm simulation to account for subject-specific lead placements, which may deviate from standard lead placements. A second plurality of surface electrode recordings corresponding to standard lead placements may also be computed based on the rhythm simulation.

In some example embodiments, a transformation matrix A may be generated based on a difference between the first plurality of surface electrode recordings and the second plurality of surface electrode recordings. The transformation matrix A may capture variations in lead placement as well as subject anatomy. Accordingly, the transformation matrix A may be applied to a clinical electrogram (e.g., a clinical electrocardiogram, a clinical electroencephalogram, and/or the like) to generate a corrected electrogram (e.g., a corrected electrogram, a corrected electroencephalogram, and/or the like) by at least removing, from the clinical electrogram, deviations that are introduced by non-standard lead placement and/or anatomical variations.

Figure 9D:
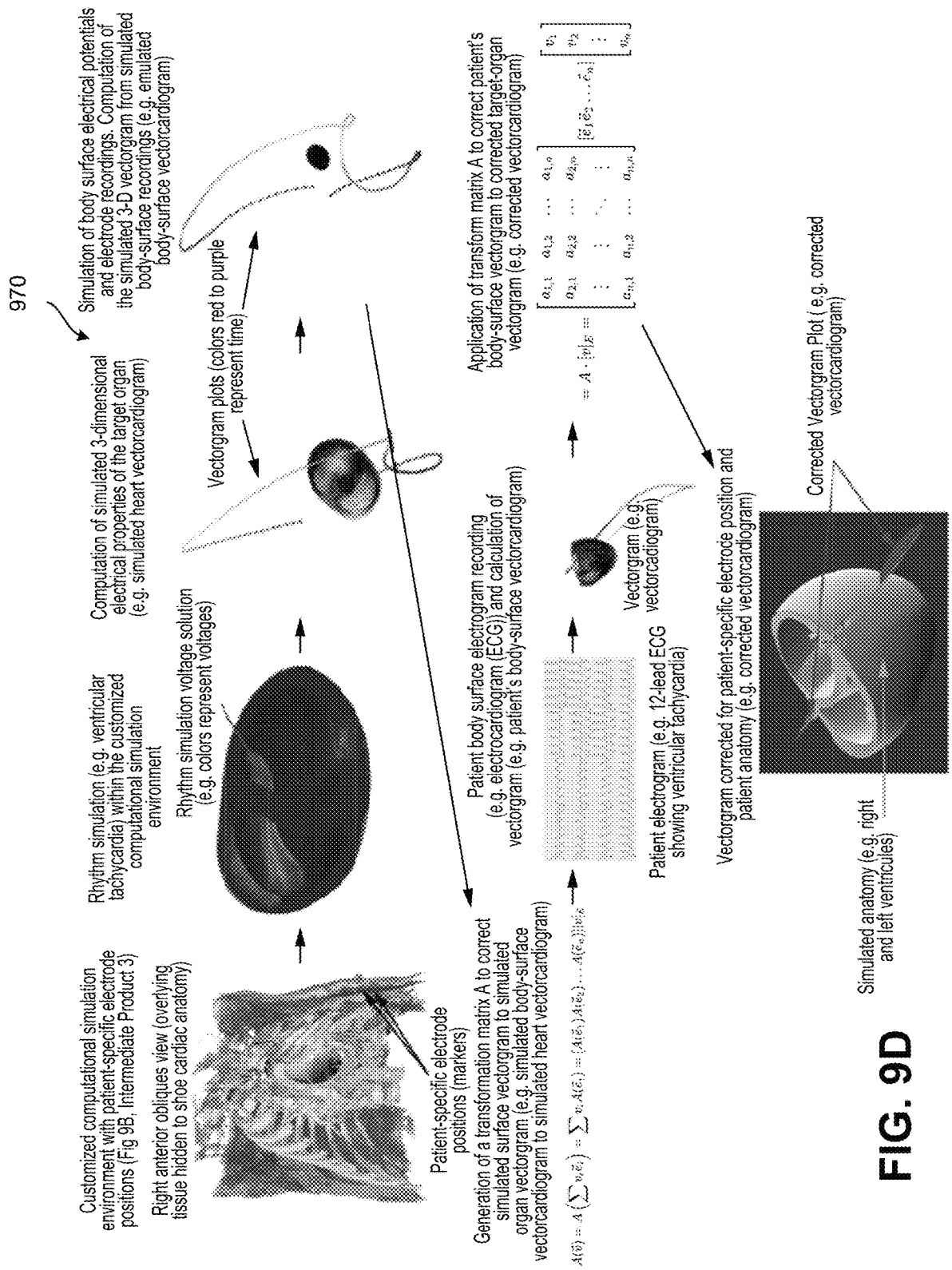
FIG. 9D depicts a diagram illustrating an example of process for generating a corrected vectorgram, in accordance with some example embodiments.

FIG. 9D a block diagram illustrating an example of process 970 for generating a corrected vectorgram, in accordance with some example embodiments. Referring to FIGS. 1 and 9D, the process 970 may be performed by the simulation controller 110 in order to generate a corrected electrogram that accounts for variations in lead placement and subject anatomy.

As shown in FIG. 9D, the simulation controller 110 may generate, based at least on a simulated three-dimensional representation of the subject's internal anatomy (e.g., thorax cavity and/or the like), a rhythm simulation (e.g., ventricular tachycardia and/or the like). The simulated three-dimensional representation of the subject's internal anatomy may be identified based on one or more clinical two-dimensional images of the subject's internal anatomy. Further based on the rhythm simulation, the simulation controller 110 may generate a simulated three-dimensional electrical properties of a target organ (e.g., heart, brain, and/or the like) as well as a simulation of body surface electrical potentials and electrical recordings. A simulated three-dimensional vectorgram (e.g., a vectorcardiogram and/or the like) may be generated based on the simulated body surface recordings.

In some example embodiments, a transformation matrix A may be generated based on a difference between the simulated three-dimensional electrical properties of the target organ and the simulated body surface recordings. The transformation matrix A may capture variations in lead placement as well as subject anatomy. Accordingly, the transformation matrix A may be applied to a clinical vectorgram (e.g., a clinical vectorcardiogram and/or the like) to generate a corrected vectorgram (e.g., a corrected vectorcardiogram and/or the like) by at least removing, from the clinical vectorcardiogram, deviations arising from non-standard lead placement and/or anatomical variations.

Figure 10:
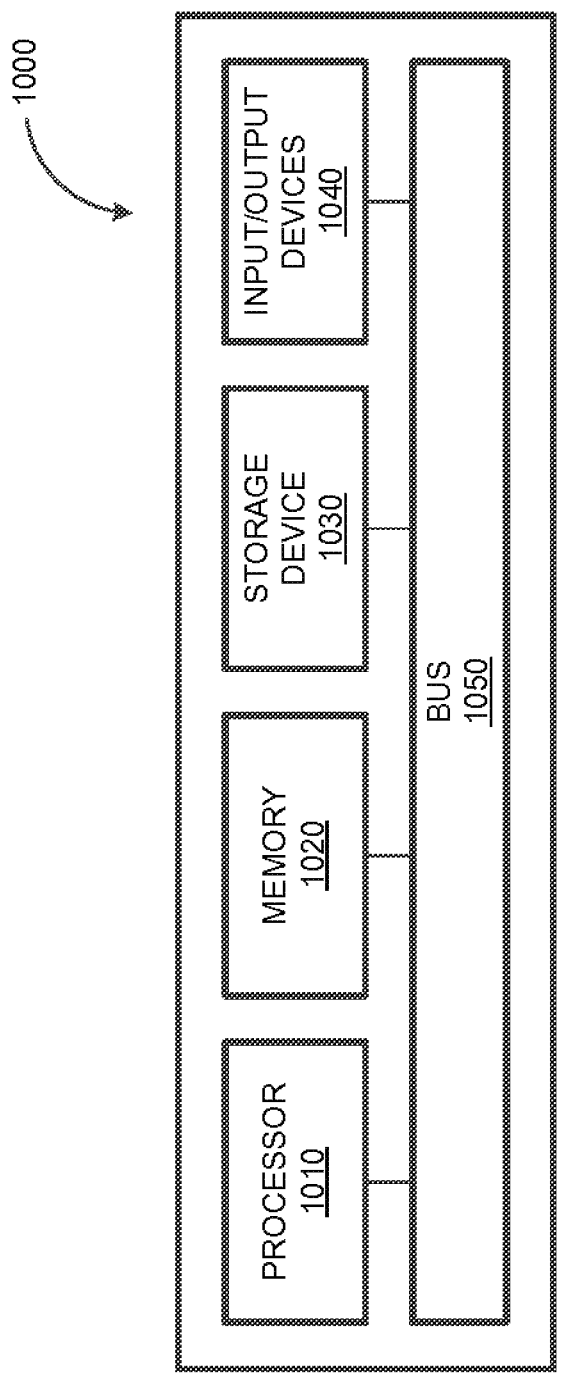
FIG. 10 depicts a block diagram illustrating a computing system, in accordance with some example embodiments.

FIG. 10 depicts a block diagram illustrating a computing system 1000, in accordance with some example embodiments. Referring to FIGS. 1 and 5, the computing system 1000 can be used to implement the simulation controller 110 and/or any components therein.

As shown in FIG. 10, the computing system 1000 can include a processor 1010, a memory 1020, a storage device 1030, and input/output device 1040. The processor 1010, the memory 1020, the storage device 1030, and the input/output device 1040 can be interconnected via a system bus 1050. The processor 1010 is capable of processing instructions for execution within the computing system 1000. Such executed instructions can implement one or more components of, for example, the simulation controller 110. In some implementations of the current subject matter, the processor 1010 can be a single-threaded processor. Alternately, the processor 1010 can be a multi-threaded processor. The processor 1010 is capable of processing instructions stored in the memory 1020 and/or on the storage device 1030 to display graphical information for a user interface provided via the input/output device 1040.

The memory 1020 is a computer readable medium such as volatile or non-volatile that stores information within the computing system 1000. The memory 1020 can store data structures representing configuration object databases, for example. The storage device 1030 is capable of providing persistent storage for the computing system 1000. The storage device 1030 can be a floppy disk device, a hard disk device, an optical disk device, or a tape device, or other suitable persistent storage means. The input/output device 1040 provides input/output operations for the computing system 1000. In some implementations of the current subject matter, the input/output device 1040 includes a keyboard and/or pointing device. In various implementations, the input/output device 1040 includes a display unit for displaying graphical user interfaces.

According to some implementations of the current subject matter, the input/output device 1040 can provide input/output operations for a network device. For example, the input/output device 1040 can include Ethernet ports or other networking ports to communicate with one or more wired and/or wireless networks (e.g., a local area network (LAN), a wide area network (WAN), the Internet).

In some implementations of the current subject matter, the computing system 1000 can be used to execute various interactive computer software applications that can be used for organization, analysis and/or storage of data in various (e.g., tabular) format. Alternatively, the computing system 1000 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, and/ or the like. The applications can include various add-in functionalities or can be standalone computing products and/or functionalities. Upon activation within the applications, the functionalities can be used to generate the user interface provided via the input/output device 1040. The user interface can be generated and presented to a user by the computing system 1000 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein.

Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one processor; and
   at least one memory including program code which when executed by the at least one processor provides operations comprising: receiving two dimensional images of an internal anatomy of a subject;
   accessing a library that maps each of a plurality of computed two-dimensional representations of a simulated three-dimensional representation to an internal anatomy that is not derived from a first subject;
   for each of a plurality of computed two-dimensional representations, generating a similarity index indicating closeness of a match between the first two-dimensional image depicting the first internal anatomy of the first subject and that computed two-dimensional representation;
   identifying a computed two-dimensional representation based on closeness of the match as indicated by the similarity index for that computed two-dimensional representation; and
   generating an output including the simulated three-dimensional representation that corresponds to the identified computed two-dimensional representation as a representation of the first internal anatomy of the first subject.

2. The system of claim 1, wherein the operations further comprise:
   generating the library including by generating, based on a first three-dimensional representation of a second internal anatomy of a second subject, the first simulated three-dimensional representation, the first simulated three-dimensional representation being generated by at least varying one or more attributes of the second internal anatomy of the second subject.

3. The system of claim 2, wherein the one or more attributes include a skeletal property, an organ geometry, a musculature, and/or a subcutaneous fat distribution.

4. The system of claim 2, wherein the library is further generated to include the first three-dimensional representation of the second internal anatomy of the second subject and/or a second three-dimensional representation of a third internal anatomy of a third subject having at least one attribute that is different from that attribute of the second internal anatomy of the second subject.

5. The system of claim 2, wherein the generating of the library further includes generating, based at least on the first simulated three-dimensional representation, the first computed two-dimensional image.

6. The system of claim 5, wherein the generating of the first computed two-dimensional image includes determining, based at least on a density and/or a transmissivity of one or more tissues included in the first simulated three-dimensional representation, a quantity of radiation able to pass through the one or more tissues included in the first simulated three-dimensional representation to form the first computed two-dimensional image.

7. The system of claim 2, wherein the first three-dimensional representation of the second internal anatomy of the second subject comprises a computed tomography (CT) scan and/or a magnetic resonance imaging (MRI) scan depicting the second internal anatomy of the second subject.

8. The system of claim 1, wherein the first simulated three-dimensional representation is further associated with a diagnosis of a condition depicted in the first simulated three-dimensional representation, and wherein the output is further generated to include the diagnosis.

9. The system of claim 1, wherein the operations further comprise:
    determining a first similarity index indicating a closeness of the match between the first computed two-dimensional image and the two-dimensional image depicting the first internal anatomy of the first subject, the first simulated three-dimensional representation identified as corresponding to the first internal anatomy of the first subject based at least on the first similarity index exceeding a threshold value and/or the first similarity index being greater than a second similarity index indicating a closeness of a match between a second computed two-dimensional image corresponding to a second simulated three-dimensional representation and the two-dimensional image depicting the first internal anatomy of the first subject.

10. The system of claim 1, wherein the first computed two-dimensional image is determined to match the two-dimensional image depicting the first internal anatomy of the first subject by at least applying an image comparison technique.

11. The system of claim 10, wherein the image comparison technique comprises scale invariant feature transform (SIFT), speed up robust feature (SURF), binary robust independent elementary features (BRIEF), and/or oriented FAST and rotated BRIEF (ORB).

12. The system of claim 10, wherein the image comparison technique comprises a machine learning model.

13. The system of claim 12, wherein the machine learning model comprises an autoencoder and/or a neural network.

14. The system of claim 1, wherein the operations further comprise:
    determining, based at least on the two-dimensional image depicting the first internal anatomy of the first subject, a lead placement for a recording device configured to measure an electrical activity of an organ, the recording device including one or more leads configured to detect a change in voltage on a body surface corresponding to the electrical activity of the organ; and
    generating, based at least on the lead placement and the first simulated three-dimensional representation of the first internal anatomy of the first subject, a simulation of the electrical activity measured by the recording device.

15. The system of claim 14, wherein the simulation of the electrical activity measured by the recording device includes a signal detected by each of the one or more leads included in the recording device.

16. The system of claim 14, wherein the recording device is configured to perform an electrocardiography (ECG) and/or an electroencephalography (EEG).

17. The system of claim 14, wherein the output is further generated to include the lead placement and/or the simulation of the electrical activity measured by the recording device.

18. The system of claim 1, wherein the identifying of the first simulated three-dimensional representation further includes eliminating a second simulated three-dimensional representation based at least on a mismatch between a demographics and/or a vital statistics of the first subject and a second subject depicted in the second simulated three-dimensional representation.

19. The system of claim 1, wherein the identifying of the first simulated three-dimensional representation further includes eliminating a second simulated three-dimensional representation based at least on a condition depicted in the second simulated three-dimensional representation being inconsistent with one or more symptoms of the first subject.

20. The system of claim 1, wherein the operations further comprise:
    providing, to a client, the output including by sending, to the client, at least a portion of the output and/or generating a user interface configured to display at least the portion of the output at the client.

21. A computer-implemented method, comprising: receiving two dimensional images of an internal anatomy of a subject;
    accessing a library including a plurality of computed two-dimensional representations corresponding to simulated three-dimensional representations of internal anatomies that are not derived from a first subject;
    for each of a plurality of computed two-dimensional representations, generating a similarity index indicating closeness of a match between the first two-dimensional image depicting the first internal anatomy of the first subject and that computed two-dimensional representation;
    identifying a computed two-dimensional representation based on closeness of the match as indicated by the similarity index for that computed two-dimensional representation; and
    generating an output including the simulated three-dimensional representation that corresponds to the identified computed two-dimensional representation as a representation of the first internal anatomy of the first subject.

22. The method of claim 21, further comprising:
    generating the library including by generating, based on a first three-dimensional representation of a second internal anatomy of a second subject, the first simulated three-dimensional representation, the first simulated three-dimensional representation being generated by at least varying one or more attributes of the second internal anatomy of the second subject.

23. The method of claim 22, wherein the one or more attributes include a skeletal property, an organ geometry, a musculature, and/or a subcutaneous fat distribution.

24. The method of claim 22, wherein the library is further generated to include the first three-dimensional representation of the second internal anatomy of the second subject and/or a second three-dimensional representation of a third internal anatomy of a third subject having at least one different attribute than the second internal anatomy of the second subject.

25. The method of claim 22, wherein the generating of the library further includes generating, based at least on the first simulated three-dimensional representation, the first computed two-dimensional image.

26. The method of claim 25, wherein the generating of the first computed two-dimensional image includes determining, based at least on a density and/or a transmissivity of one or more tissues included in the first simulated three-dimensional representation, a quantity of radiation able to pass through the one or more tissues included in the first simulated three-dimensional representation to form the first computed two-dimensional image.

27. The method of claim 22, wherein the first three-dimensional representation of the second internal anatomy of the second subject comprises a computed tomography (CT) scan and/or a magnetic resonance imaging (MRI) scan depicting the second internal anatomy of the second subject.

28. The method of claim 21, wherein the first simulated three-dimensional representation is further associated with a diagnosis of a condition depicted in the first simulated three-dimensional representation, and wherein the output is further generated to include the diagnosis.

29. The method of claim 21, further comprising:
determining a first similarity index indicating a closeness of the match between the first computed two-dimensional image and the two-dimensional image depicting the first internal anatomy of the first subject, the first simulated three-dimensional representation identified as corresponding to the first internal anatomy of the first subject based at least on the first similarity index exceeding a threshold value and/or the first similarity index being greater than a second similarity index indicating a closeness of a match between a second computed two-dimensional image corresponding to a second simulated three-dimensional representation and the two-dimensional image depicting the first internal anatomy of the first subject.

30. The method of claim 21, wherein the first computed two-dimensional image is determined to match the two-dimensional image depicting the first internal anatomy of the first subject by at least applying an image comparison technique.

31. The method of claim 30, wherein the image comparison technique comprises scale invariant feature transform (SIFT), speed up robust feature (SURF), binary robust independent elementary features (BRIEF), and/or oriented FAST and rotated BRIEF (ORB).

32. The method of claim 30, wherein the image comparison technique comprises a machine learning model.

33. The method of claim 32, wherein the machine learning model comprises an autoencoder and/or a neural network.

34. The method of claim 21, further comprising:
determining, based at least on the two-dimensional image depicting the first internal anatomy of the first subject, a lead placement for a recording device configured to measure an electrical activity of an organ, the recording device including one or more leads configured to detect a change in voltage on a body surface corresponding to the electrical activity of the organ; and
generating, based at least on the lead placement and the first simulated three-dimensional representation of the first internal anatomy of the first subject, a simulation of the electrical activity measured by the recording device.

35. The method of claim 34, wherein the simulation of the electrical activity measured by the recording device includes a signal detected by each of the one or more leads included in the recording device.

36. The method of claim 34, wherein the recording device is configured to perform an electrocardiography (ECG) and/or an electroencephalography (EEG).

37. The method of claim 34, wherein the output is further generated to include the lead placement and/or the simulation of the electrical activity measured by the recording device.

38. The method of claim 21, wherein the identifying of the first simulated three-dimensional representation further includes eliminating a second simulated three-dimensional representation based at least on a mismatch between a demographics and/or a vital statistics of the first subject and a second subject depicted in the second simulated three-dimensional representation.

39. The method of claim 21, wherein the identifying of the first simulated three-dimensional representation further includes eliminating a second simulated three-dimensional representation based at least on a condition depicted in the second simulated three-dimensional representation being inconsistent with one or more symptoms of the first subject.

40. The method of claim 21, further comprising:
providing, to a client, the output including by sending, to the client, at least a portion of the output and/or generating a user interface configured to display at least the portion of the output at the client.

41. A non-transitory computer readable medium storing instructions, which when executed by at least one data processor, result in operations comprising: receiving two dimensional images of an internal anatomy of a subject;
accessing a library including a plurality of computed two-dimensional representations corresponding to simulated three-dimensional representations of internal anatomies that are not derived from a first subject;
for each of a plurality of computed two-dimensional representations, generating a similarity index indicating closeness of a match between the first two-dimensional image depicting the first internal anatomy of the first subject and that computed two-dimensional representation;
identifying a computed two-dimensional representation based on closeness of the match as indicated by the similarity index for that computed two-dimensional representation; and
generating an output including the simulated three-dimensional representation that corresponds to the identified computed two-dimensional representation as a representation of the first internal anatomy of the first subject.

42. An apparatus, comprising: receiving two dimensional images of an internal anatomy of a subject;
a library including a plurality of computed two-dimensional representations corresponding to simulated three-dimensional representations of internal anatomies that are not derived from a first subject; and
means for, for each of a plurality of computed two-dimensional representations, generating a similarity index indicating closeness of a match between the first two-dimensional image depicting the first internal anatomy of the first subject and that computed two-dimensional representation;
means for identifying a computed two-dimensional representation based on closeness of the match as indicated by the similarity index for that computed two-dimensional representation; and
means for generating an output including the simulated three-dimensional representation that corresponds to the identified computed two-dimensional representation as a representation of the first internal anatomy of the first subject.

43. A computer-implemented method, comprising: receiving two dimensional images of an internal anatomy of a subject;
- identifying, in a library including a plurality of computed two-dimensional representations corresponding to simulated three-dimensional representations of internal anatomies that are not derived from a first subject, a first simulated three-dimensional representation corresponding to a first internal anatomy of the first subject, the first simulated three-dimensional representation being identified based at least on a match between the first computed two-dimensional image corresponding to the first simulated three-dimensional representation and a two-dimensional image depicting the first internal anatomy of the first subject; and
- generating an output including the simulated three-dimensional representation of the first internal anatomy of the first subject
- wherein the first computed two-dimensional image is generated based on a quantity of radiation able to pass through one or more tissues included in the first simulated three-dimensional representation to form the first computed two-dimensional image based at least on a density and/or a transmissivity of the one or more tissues included in the first simulated three-dimensional representation.

* * * * *

UNITED STATES PATENT AND TRADEMARK OFFICE
CERTIFICATE OF CORRECTION

| | |
|---|---|
| PATENT NO. | : 11,475,570 B2 |
| APPLICATION NO. | : 16/785530 |
| DATED | : October 18, 2022 |
| INVENTOR(S) | : David Krummen et al. |

It is certified that error appears in the above-identified patent and that said Letters Patent is hereby corrected as shown below:

In the Claims

In Column 32, Line 47, delete "receiving" and insert -- means for receiving --.

Signed and Sealed this
Second Day of July, 2024

*Katherine Kelly Vidal*

Katherine Kelly Vidal
*Director of the United States Patent and Trademark Office*